(12) United States Patent
Thornton et al.

(10) Patent No.: US 11,426,304 B2
(45) Date of Patent: Aug. 30, 2022

(54) ORAL APPLIANCE

(71) Applicant: Airway Technologies, LLC, Carrollton, TX (US)

(72) Inventors: W. Keith Thornton, Dallas, TX (US); Alastair McAuley, Auckland (NZ)

(73) Assignee: AirWay Technologies, LLC, Farmers Branch, TX (US)

( * ) Notice: Subject to any disclaimer, the term of this patent is extended or adjusted under 35 U.S.C. 154(b) by 478 days.

(21) Appl. No.: 16/427,524

(22) Filed: May 31, 2019

(65) Prior Publication Data

US 2019/0282392 A1    Sep. 19, 2019

Related U.S. Application Data

(63) Continuation of application No. 14/931,942, filed on Nov. 4, 2015, now Pat. No. 10,376,408, which is a
(Continued)

(51) Int. Cl.
*A61F 5/56* (2006.01)
*A61B 5/00* (2006.01)
(Continued)

(52) U.S. Cl.
CPC .............. *A61F 5/566* (2013.01); *A61B 5/01* (2013.01); *A61B 5/02438* (2013.01);
(Continued)

(58) Field of Classification Search
CPC ... A61F 5/566; A61F 5/56; A61F 5/50; A63B 71/085; A63B 2071/088; A63B 2208/12;
(Continued)

(56) References Cited

U.S. PATENT DOCUMENTS 690,663 A    1/1902  Pratt
746,869 A   12/1903  Moulton
(Continued)

FOREIGN PATENT DOCUMENTS

DE    2 320 501    11/1974
DE   29506512.5    7/1995
(Continued)

OTHER PUBLICATIONS

Indian Office Action; Appl. No. 201717006216; 7 pages, dated Feb. 27, 2020
(Continued)

*Primary Examiner* — Ophelia A Hawthorne
(74) *Attorney, Agent, or Firm* — Patterson + Sheridan, LLP

(57) ABSTRACT

An oral appliance includes an upper arch, a lower arch, and an electronic device. The upper arch is configured to be positioned within a user's mouth proximate the user's maxillary dentition when the upper arch is positioned in the user's mouth. The lower arch is configured to be positioned proximate the user's mandibular dentition when the lower arch is positioned in the user's mouth. The electronic device is coupled to one or more of the upper arch and the lower arch, the electronic device configured to monitor a feature of the environment proximate one or more of the upper arch and the lower arch.

11 Claims, 27 Drawing Sheets

Related U.S. Application Data continuation-in-part of application No. 14/834,149, filed on Aug. 24, 2015, now abandoned.

(60) Provisional application No. 62/041,486, filed on Aug. 25, 2014.

(51) Int. Cl.
- *A61B 5/145* (2006.01)
- *A61B 5/087* (2006.01)
- *A61B 5/11* (2006.01)
- *A61B 5/01* (2006.01)
- *A61B 5/024* (2006.01)

(52) U.S. Cl.
CPC ............... *A61B 5/087* (2013.01); *A61B 5/11* (2013.01); *A61B 5/14542* (2013.01); *A61B 5/4833* (2013.01); *A61B 5/682* (2013.01)

(58) Field of Classification Search
CPC ..... A63B 2071/086; A61B 13/00; A61C 7/08; A61C 5/14; A61C 7/00
See application file for complete search history.

(56) References Cited

U.S. PATENT DOCUMENTS

| | | |
|---|---|---|
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,833,278 A | 5/1958 | Ross |
| 2,867,212 A | 1/1959 | Nunn, Jr. |
| 2,882,893 A | 4/1959 | Godfrey |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Comiello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick |
| 3,522,805 A | 8/1970 | Wallshein |
| 3,690,004 A | 9/1972 | Frush |
| 3,054,208 A | 12/1974 | Arant |
| 3,064,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud |
| 4,258,710 A | 3/1981 | Reber |
| 4,289,127 A | 9/1981 | Nelson |
| 4,304,227 A | 12/1981 | Samelson |
| 4,376,628 A | 3/1983 | Aardse |
| 4,382,783 A | 5/1983 | Rosenberg |
| 4,419,992 A | 12/1983 | Chorbajian |
| 4,433,956 A | 2/1984 | Witzig |
| 4,439,147 A | 3/1984 | Magill |
| 4,439,149 A | 3/1984 | Devincenzo |
| 4,454,090 A | 6/1984 | Saumell |
| 4,495,945 A | 1/1985 | Liegner |
| 4,505,672 A | 3/1985 | Kurz |
| 4,530,662 A | 7/1985 | Andersson |
| 4,553,549 A | 11/1985 | Pope |
| 4,568,280 A | 2/1986 | Ahlin |
| 4,569,342 A | 2/1986 | von Nostitz |
| 4,593,686 A | 6/1986 | Lloyd |
| 4,602,905 A | 7/1986 | O'Keefe, III |
| 4,639,220 A | 1/1987 | Nara |
| 4,668,188 A | 5/1987 | Wolfenson |
| 4,669,459 A | 6/1987 | Spiewak |
| 4,676,240 A | 6/1987 | Gardy |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,862,903 A | 9/1989 | Campbell |
| 4,892,478 A | 1/1990 | Tateosian |
| 4,901,737 A | 2/1990 | Toone |
| 4,932,867 A | 6/1990 | Ueno |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman |
| 5,028,232 A | 7/1991 | Snow |
| 5,040,976 A | 8/1991 | Ubel, III |
| 5,042,506 A | 8/1991 | Liberati |
| 5,046,512 A | 9/1991 | Marchie |
| 5,052,409 A | 10/1991 | Tepper |
| 5,055,039 A | 10/1991 | Abbatie |
| 5,056,534 A | 10/1991 | Wright |
| 5,064,371 A | 11/1991 | Smeltzer |
| 5,066,231 A | 11/1991 | Oxman |
| 5,078,600 A | 1/1992 | Austin |
| 5,092,346 A | 3/1992 | Hays |
| 5,103,838 A | 4/1992 | Yousif |
| 5,112,225 A | 5/1992 | Diesso |
| 5,117,816 A | 6/1992 | Shapiro |
| 5,154,184 A | 10/1992 | Alvarez |
| 5,154,609 A | 10/1992 | George |
| 5,183,057 A | 2/1993 | Syrop |
| 5,188,529 A | 2/1993 | Lüth |
| 5,190,457 A | 3/1993 | Schreinemakers |
| 5,213,498 A | 5/1993 | Pelerin |
| 5,265,595 A | 11/1993 | Rudolph |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen |
| 5,365,945 A | 11/1994 | Halstrom |
| 5,370,533 A | 12/1994 | Bushnell |
| 5,373,859 A | 12/1994 | Forney |
| 5,409,017 A | 4/1995 | Lowe |
| 5,415,544 A | 5/1995 | Oxman |
| 5,427,117 A | 6/1995 | Thornton |
| 5,474,060 A | 12/1995 | Evans |
| 5,499,633 A | 3/1996 | Fenton |
| 5,503,552 A | 4/1996 | Diesso |

(56) References Cited

U.S. PATENT DOCUMENTS

| | | |
|---|---|---|
| 5,537,994 A | 7/1996 | Thornton |
| 5,551,872 A | 9/1996 | Mena |
| 5,562,449 A | 10/1996 | Jacobs |
| 5,566,683 A | 10/1996 | Thornton |
| 5,570,704 A | 11/1996 | Buzzard |
| 5,582,517 A | 12/1996 | Adell |
| 5,678,567 A | 10/1997 | Thornton |
| 5,681,164 A | 10/1997 | Bass |
| 5,718,244 A | 2/1998 | Thornton |
| 5,720,302 A | 2/1998 | Belfer |
| 5,755,219 A | 5/1998 | Thornton |
| 5,807,100 A | 9/1998 | Thornton |
| 5,829,441 A | 11/1998 | Kidd |
| 5,846,082 A | 12/1998 | Thornton |
| 5,891,372 A | 4/1999 | Besset |
| 5,954,048 A | 9/1999 | Thornton |
| 5,983,892 A | 11/1999 | Thornton |
| 6,012,919 A | 1/2000 | Cross, III |
| 6,083,442 A | 7/2000 | Gabilly |
| 6,109,265 A | 8/2000 | Frantz |
| 6,155,262 A | 12/2000 | Thornton |
| 6,209,542 B1 | 4/2001 | Thornton |
| 6,247,926 B1 | 6/2001 | Thornton |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,450,167 B1 | 9/2002 | David |
| 6,464,924 B1 | 10/2002 | Thornton |
| 6,516,805 B1 | 2/2003 | Thornton |
| 6,536,439 B1 | 3/2003 | Palmisano |
| 6,571,798 B1 | 6/2003 | Thornton |
| 6,604,527 B1 | 8/2003 | Palmisano |
| 6,675,802 B1 | 1/2004 | Thornton |
| 6,758,212 B2 | 7/2004 | Swann |
| 6,769,910 B1 | 8/2004 | Pantino |
| 6,845,774 B2 | 1/2005 | Gaskell |
| 6,877,513 B2 | 4/2005 | Scarberry |
| 7,174,895 B2 | 2/2007 | Thornton |
| 7,597,103 B2 | 10/2009 | Thornton |
| 7,650,885 B2 | 1/2010 | Paoluccio |
| 7,677,889 B2 | 3/2010 | Thornton |
| 7,721,741 B2 | 5/2010 | Thornton |
| 7,748,386 B2 | 7/2010 | Thornton |
| 7,823,590 B2 | 11/2010 | Bibi et al. |
| 7,832,403 B2 | 11/2010 | Halstrom |
| 7,909,035 B2 | 3/2011 | Thornton |
| 8,020,276 B2 | 9/2011 | Thornton |
| 2002/0000230 A1 | 1/2002 | Gaskell |
| 2002/0139366 A1 | 10/2002 | Gaschke |
| 2003/0217753 A1 | 11/2003 | Thornton |
| 2003/0234022 A1 | 12/2003 | Belfer |
| 2004/0079374 A1 | 4/2004 | Thornton |
| 2004/0226563 A1 | 11/2004 | Xu |
| 2004/0237965 A1 | 12/2004 | Bibi |
| 2005/0028827 A1 | 2/2005 | Halstrom |
| 2005/0034733 A1 | 2/2005 | Liddle et al. |
| 2005/0268914 A1 | 12/2005 | Paoluccio |
| 2007/0125388 A1 | 6/2007 | Thornton |
| 2007/0235037 A1 | 10/2007 | Thornton |
| 2008/0006273 A1 | 1/2008 | Thornton |
| 2008/0006274 A1 | 1/2008 | Thornton |
| 2008/0032256 A1 | 2/2008 | Thornton |
| 2008/0127984 A1 | 6/2008 | Thornton |
| 2008/0295850 A1 | 12/2008 | Lesniak |
| 2009/0014013 A1 | 1/2009 | Magnin |
| 2009/0130624 A1 | 5/2009 | Sun |
| 2010/0065067 A1 | 3/2010 | Lee |
| 2010/0263677 A1 | 10/2010 | Thornton |
| 2011/0114099 A1 | 5/2011 | Goldstein |
| 2011/0168187 A1 | 7/2011 | Nelissen |
| 2011/0315141 A1 | 12/2011 | Lavi et al. |
| 2012/0255560 A1* | 10/2012 | Thornton ............... A61F 5/566 128/848 |
| 2013/0023797 A1 | 1/2013 | Hanewinkel et al. |
| 2013/0112210 A1* | 5/2013 | Stein ............... A61F 5/566 128/848 |
| 2013/0263865 A1* | 10/2013 | Khast ............... A61F 5/566 128/848 |
| 2014/0053852 A1 | 2/2014 | Thornton |
| 2014/0152464 A1 | 6/2014 | Smith |
| 2014/0350354 A1 | 11/2014 | Stenzler et al. |

FOREIGN PATENT DOCUMENTS

| | | |
|---|---|---|
| EP | 0 312 368 | 4/1989 |
| EP | 0 359 135 | 3/1990 |
| GB | 1 569 129 | 6/1980 |
| GB | 2 072 567 | 10/1981 |
| WO | WO 91/12777 | 9/1991 |
| WO | WO 97/25010 | 7/1997 |
| WO | WO 98/26736 | 6/1998 |
| WO | WO 98/43177 | 10/1998 |
| WO | 2007146523 A2 | 12/2007 |
| WO | WO 2007/146523 A2 | 12/2007 |
| WO | WO 2014/110548 A4 | 7/2014 |

OTHER PUBLICATIONS

PCT Notification of Transmittal of the International Search Report and the Written Opinion of the International Searching Authority, or the Declaration; dated Jul. 13, 2012; International app No. PCT/US2012/032407; 18 pages.

PCT Notification of Transmittal of the International Search Report and the Written Opinion of the International Searching Authority, or the Declaration; dated Jul. 17, 2012; International app. No. PCT/US2012/028885; 18 pages.

PCT Intl. Searching Authority, Invitation to pay Add'l Fees, Re PCT/US2012/028885 dated May 30, 2012 (0306 Foreign).

PCT Intl. Searching Authority, Invitation to pay Add'l Fees, Re PCT/US2012/032407 dated May 30, 2012 (0314 Foreign).

Personally Moulded Sleep Apnea Masks, http:/;web.archive.org/web/20030618145716/www.sleepapneamasks.com.au/default.asp, downloaded Aug. 17, 2009 (2 pages).

European Patent Office, Application No. 03 809 555.0-125, Applicant: W. Keith Thornton, 4 pages, Aug. 7, 2009.

PCT, Notification of Transmittal of the International Search Report and the Written Opinion of the International Searching Authority, or the Declaration, International Application No. PCT/US2011/039231, filing date Jun. 6, 2011 (11 pgs).

Japanese Patent Office, Action re patent application 2004/500750, dated Oct. 14, 2008.

Austrailian Office Action re patent application No. 2007/243957 dated Mar. 9, 2012.

Canadian IPO patent application No. 2,502,280 dated Feb, 23, 2010.

Mayo Clinic Health Letter; Reliable Information for a Healthier Life; Snoring: Laser Surgery Joins Battle to Restore Peace and Quiet; vol. 13, No. 7, 8 pages, Jul. 1995.

Photocopies of 2-piece dental device manufactured by Currie-Gibson Dental Laboratory, Inc., prior to Apr. 13, 1993, 5 pages.

Farrar, et al, A Clinical Outline of Temporomandibular Joint Diagnosis and Treatment, Normandie Study Group for TMJ Dysfunction, 3 pages, 1983.

Professional Positioners; Dedicated to Excellence brochure, 3 pages.

Great Lakes Orthodontics, Ltd.; Noctural Airway Patency Appliance; 2 pages.

Schmidt-Nowara, et al.; An American Sleep Disorders Association Review; Oral Appliances for the Treatment of Snoring and Obstructive Sleep Apnea: A Review; pp. 501-510, 1995.

George, Peter; Treatment of Snoring and Obstructive Sleep Apnea with a Dental Device; 5 pages, Jul.-Aug. 1993.

Database WOI, Section PQ, Week 9039, Derwent Publications, Ltd., London, GB; XP-002116355 Abstract—Surgical Mouth Air Duct; 1 page, Dec. 15, 1989.

PCT Notification of Transmittal of the International Search Report or the Declaration for International Application No. PCT/US97/08708, dated Aug. 12, 1997.

(56) References Cited

OTHER PUBLICATIONS

PCT Invitation to Pay Additional Fees for International Application No. PCT/US03/13705, dated Oct. 10, 2003.

PCT, Notification of Transmittal of the International Search Report and Written Opinion of the International Searching Authority, or the Declaration, PCT/US07/02736, 10 pages, dated Oct. 26, 2007.

PCT, Notification of Transmittal of the International Search Report and the Written Opinion of the Internation Searching Authority, or the Declaration, PCT/US2010/051136, 10 pages, dated Mar. 4, 2011.

Craig, William H., et al.; "Skeletal class II treatment with the Chateau appliance," The Journal of Pedodontics (vol. 11:120); pp. 120-138, 1987.

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages, Oct. 2008.

European Patent Office; Communication pursuant to Rule 62 EPC; Appl. No. 15834961.3-1122/3185823, dated Jun. 14, 2018.

PCT, Notification of Transmittal of the International Search Report and the Written Opinion of the International Searching Authority, or the Declaration, PCT/US2016/059056; dated Mar. 15, 2017.

PCT Invitation to Pay Additional Fees; Intl. App. No. PCT/US2016/059056; dated Jan. 2, 2017.

PCT, Notification of Transmittal of the International Search Report and the Written Opinion of the International Searching Authority, or the Declaration, PCT/US2015/046709, dated Jan. 20, 2016.

Intellectual Property India Examination Report for Application No. 201817013795 dated Jun. 10, 2020.

Communication pursuant to Article 94(3) EPC; Appln No. 15 834 961.3-1122; 5 pages, dated May 29, 2020.

\* cited by examiner

ORAL APPLIANCE

CROSS REFERENCE TO RELATED APPLICATIONS

This application is a continuation of U.S. application Ser. No. 14/931,942 entitled "Oral Application," filed Nov. 4, 2015 which is a continuation-in-part of U.S. application Ser. No. 14/834,149, entitled "Oral Appliance," which was filed Aug. 24, 2015, which claims the benefit of U.S. Provisional Application Ser. No. 62/041,486, entitled "Oral Appliance," which was filed Aug. 25, 2014, having common inventorship, the entire contents of which are incorporated herein by reference.

TECHNICAL FIELD

This invention relates generally to medical and dental devices, and more particularly to an apparatus for prevention of snoring and improved breathing.

BACKGROUND

Many people experience difficulty sleeping because of breathing problems. These problems may result in snoring, or the more serious condition of sleep apnea. One treatment for sleep breathing disorders involves the use of dental devices for extending forward the lower jaw of the patient. These devices operate to more fully open the breathing passageway, thereby allowing for easier breathing.

SUMMARY OF THE DISCLOSURE

In one embodiment, an oral appliance includes an upper arch, a lower arch, and an electronic device. The upper arch is configured to be positioned within a user's mouth proximate the user's maxillary dentition when the upper arch is positioned in the user's mouth. The lower arch is configured to be positioned proximate the user's mandibular dentition when the lower arch is positioned in the user's mouth. The electronic device is coupled to one or more of the upper arch and the lower arch, the electronic device configured to monitor a feature of the environment proximate one or more of the upper arch and the lower arch.

In another embodiment, an apparatus includes an arched seal and an electronic device. The arched seal includes a flexible material and is configured to engage one or more of an upper arch and a lower arch of an oral appliance. The arched seal is also configured to be positioned between a user's dentition and the user's lips when the oral appliance is positioned in the user's mouth. The arched seal is further configured to inhibit the user's breathing through the user's mouth when the arched seal is positioned in the user's mouth. The arched seal is also configured to extend beyond the cuspids of the user's dentition when the arched seal is positioned in the user's mouth. The electronic device is coupled to the arched seal, the electronic device configured to monitor a feature of the environment proximate the arched seal.

In another embodiment, an oral appliance includes an upper arch, a lower arch, a coupler, a seal, and an electronic device. The upper arch is configured to be positioned within a user's mouth proximate the user's maxillary dentition when the upper arch is positioned in the user's mouth. The upper arch includes a first upper attachment point and a second upper attachment point. The first attachment point and the second attachment point are positioned, with respect to each other, on opposite sides of a plane substantially bisecting the upper arch. The lower arch is configured to be positioned proximate the user's mandibular dentition when the lower arch is positioned in the user's mouth. The coupler is configured to couple the upper arch to the lower arch and to establish a position of the user's mandibular arch relative to the user's maxillary arch when the upper and lower arches are positioned in the user's mouth. The seal is configured to couple to the upper arch at the first and second upper attachment points to inhibit breathing through the user's mouth when the oral appliance is positioned in the user's mouth. A first portion of the seal configured to be positioned proximate the upper arch is thicker than a second portion of the seal configured to be positioned proximate the lower arch to allow the lower arch to move relative to the upper arch when the upper arch and the lower arch are positioned in the user's mouth. The seal is configured to be positioned between the user's dentition and the user's lips when the oral appliance is positioned in the user's mouth to inhibit breathing through the user's mouth. The electronic device is coupled to the seal. The electronic device is configured to monitor one or more of a temperature, a movement, an air flow, a pulse, and a blood oxygen level.

Certain embodiments may provide one or more technical advantages. A technical advantage of an embodiment includes providing space for the tongue to rest behind the maxillary incisors when the oral appliance is positioned in a user's mouth. A technical advantage of one embodiment includes improved structural support for the second arched frame. A technical advantage of one embodiment includes improved flexibility of the oral appliance when molding for a user's teeth. A technical advantage of one embodiment includes inhibiting the flow of air through a user's mouth. Another technical advantage of one embodiment includes reduced snoring. A technical advantage of an embodiment includes allowing for monitoring of certain environmental and/or biological features proximate an oral appliance so that the oral appliance may be adjusted based on that monitoring. Certain embodiments may provide one or more of these advantages while minimizing, eliminating, or preventing a portion of an oral appliance or seal from protruding outside a user's mouth past the lips. Certain embodiments of the invention may include none, some, or all of the above technical advantages. One or more other technical advantages may be readily apparent to one skilled in the art from the figures, descriptions, and claims included herein.

BRIEF DESCRIPTION OF THE FIGURES

For a more complete understanding of the present invention and its features and advantages, reference is now made to the following description, taken in conjunction with the accompanying drawings, in which.

DETAILED DESCRIPTION OF THE FIGURES

Figure 1A:
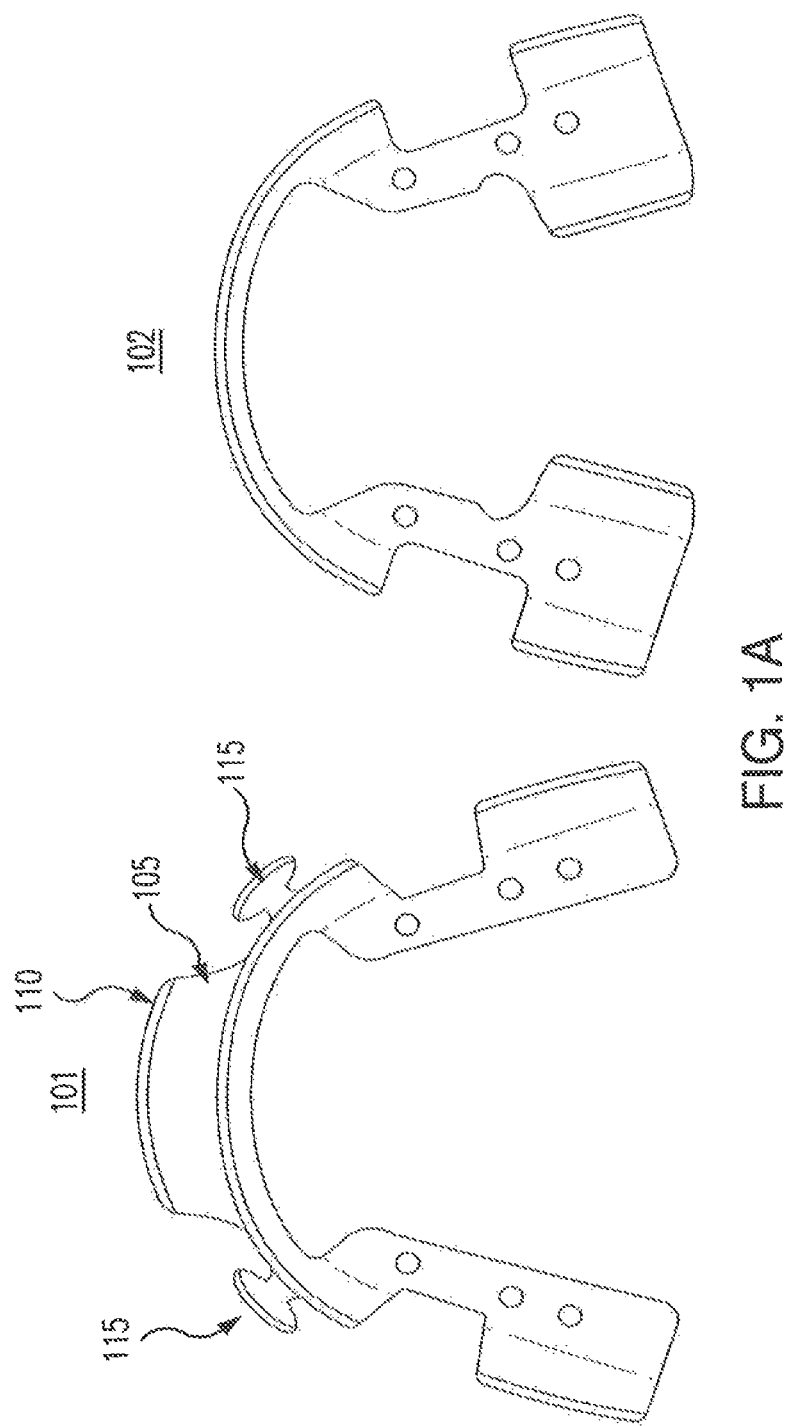
FIG. 1A shows an upper arched frame and a lower arched frame.

Embodiments of the present invention and its advantages are best understood by referring to FIGS. 1A through 6B, like numerals being used for like and corresponding parts of the various drawings.

Oral appliances may alleviate snoring while a user is sleeping. For example, oral appliances may include mechanisms that push or pull on the user's lower jaw to open the user's breathing passageways, which may reduce snoring. Oral appliances may also help treat more serious conditions such as sleep apnea. In a particular embodiment, an oral appliance may be configured to allow a space behind the maxillary incisors in which a user's tongue can rest when the oral appliance is positioned in the user's mouth.

Oral appliances may include an upper arch and a lower arch. The upper arch may be fit for the user's upper dental arch (maxillary arch). The lower arch may be fit for the user's lower dental arch (mandibular arch). The positioning of the arches in the user's mouth may be adjusted to adjust the forward position of the user's jaw. By changing the position of the jaw, snoring and sleep apnea may be treated.

Each arch may include an arched frame and a moldable tray coupled to the arched frame. The arched frame provides structural support. The moldable tray may be heated and molded to conform to the user's teeth. In this manner, the arch may be configured to fit comfortably over the user's teeth when the oral appliance is positioned in the user's mouth.

A seal may be configured to engage the oral appliance to inhibit the flow of air through the user's mouth. The seal may rest in the region between the user's teeth and the user's lips when positioned in the user's mouth. As a result, the seal may encourage the user to breathe through his nose when the oral appliance is positioned in the users mouth, which may prevent drooling and may prevent the user's mouth from drying. The seal and/or oral appliance may reduce snoring when they are positioned in the user's mouth. The seal is beneficial when used with a CPAP system that delivers a flow of gas to a user's nasal passage. Additional description of oral appliances and CPAP systems may be found in U.S. patent application Ser. No. 14/226,968 and U.S. patent application Ser. No. 14/009,821, both of which are hereby incorporated by reference.

Sometimes, oral appliances and/or seals may protrude from the user's mouth when the user is wearing the oral appliance and/or seal. Some users may find these protrusions to be undesirable because of the negative effect on their appearance. Certain oral appliances and seals disclosed herein may be configured to minimize, eliminate, or prevent certain portions of the oral appliance and/or seal from protruding out of or extending beyond the user's lips. In this manner, the user's cosmetic appearance may not be negatively affected when wearing the oral appliance and/or seal.

FIGS. 1A-1G show an oral appliance that may minimize, eliminate, or prevent protrusions from the user's mouth when the oral appliance is positioned in the user's mouth. FIGS. 2A-2E show a seal that couples to the oral appliance. The seal may also minimize, eliminate, or prevent protrusions from the user's mouth when the seal and oral appliance are positioned in the user's mouth.

Figure 6A:
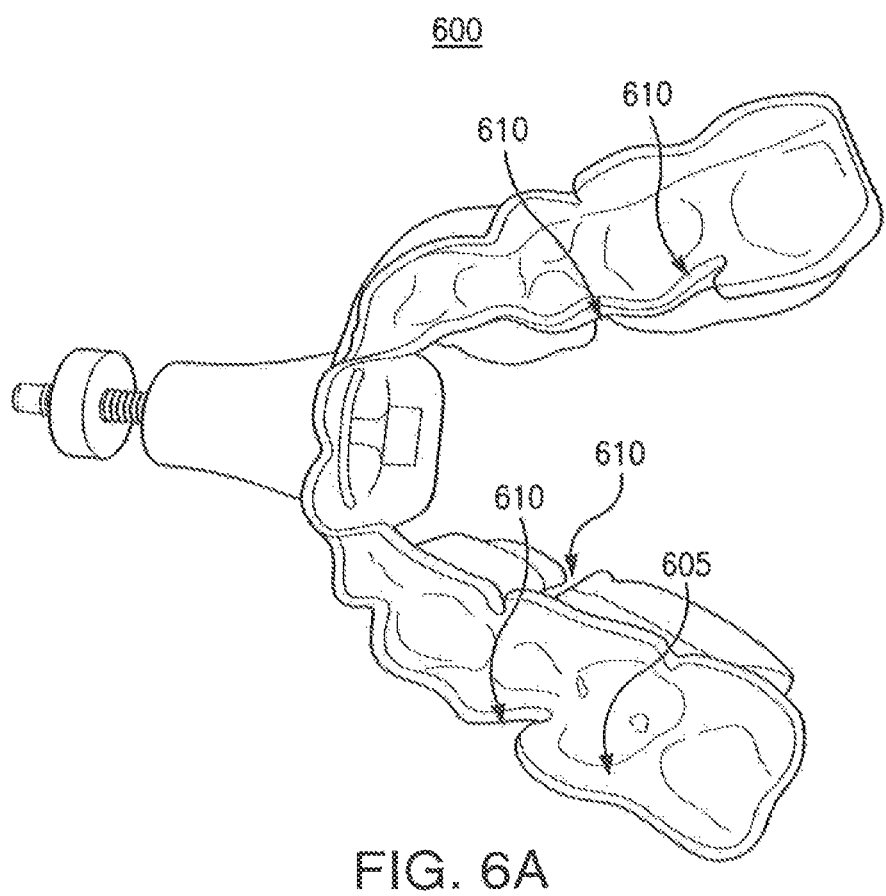
FIGS. 6A-B show an oral appliance.
Figure 6B:
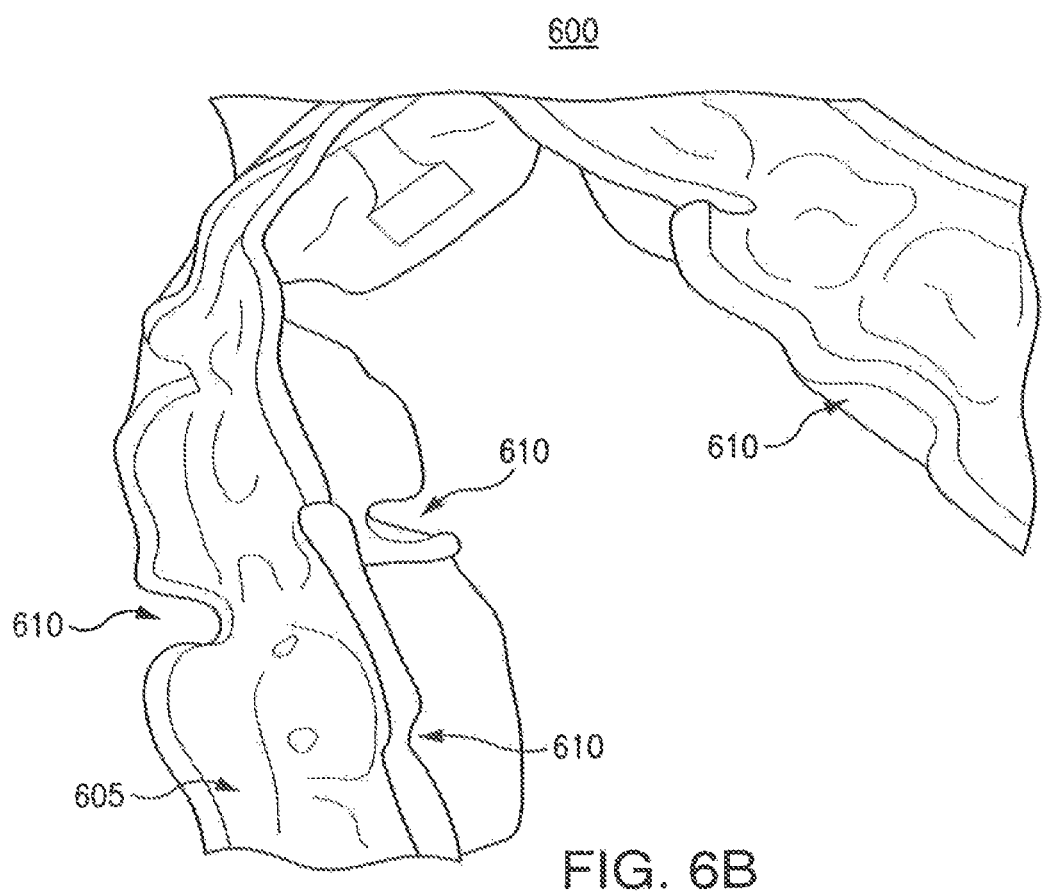

FIGS. 3A-3F show an oral appliance that has an adjustable coupler. By adjusting the position of the coupler, the forward position of the user's jaw may be adjusted when the oral appliance is positioned in the user's mouth. FIGS. 4A-5D show a seal and an oral appliance. The seal may couple to the oral appliance by engaging a post of the oral appliance. The seal may include an electronic compliance monitor. FIGS. 6A-6B show an oral appliance with slots that improve the flexibility of the oral appliance.

Although different features are shown in different figures, this disclosure contemplates any illustrated embodiment including any feature shown in any figure. For example, the slots shown in FIGS. 6A-6B may be incorporated into any of the oral appliance shown in FIGS. 1A-1G. As another example, the electronic compliance monitor shown in FIGS. 4A-5D may be incorporated into the seal shown in FIGS. 2A-2E.

FIGS. 1A-1G show an oral appliance. The oral appliance may be positioned in a user's mouth to adjust the forward position of the user's jaw while sleeping. In certain embodiments, the oral appliance may be configured to minimize, eliminate and/or prevent certain portions of the oral appliance from protruding out of the user's mouth when the oral appliance is positioned in the user's mouth. The oral appliance may include an upper arch, a lower arch, and a coupler. The upper arch and lower arch may each include an arched frame and a moldable tray.

FIG. 1A shows an upper arched frame 101 and a lower arched frame 102. The upper arched frame 101 and the lower arched frame 102 may provide structural support for the upper arch and the lower arch. Upper arched frame 101 and lower arched frame 102 may both include an arched body that is configured to receive a moldable tray. Shelf 105 and attachment points 115 may be coupled to the arched body of upper arched frame 101. Ridge 110 may be coupled to shelf 105. In certain embodiments, both upper arched frame 101 and lower arched frame 102 may include polycarbonate or any similar semi-rigid thermoplastic that can withstand 100 degrees Celsius without deforming, such as for example, nylon and/or polycarbonate resin thermoplastic.

Figure 1B:
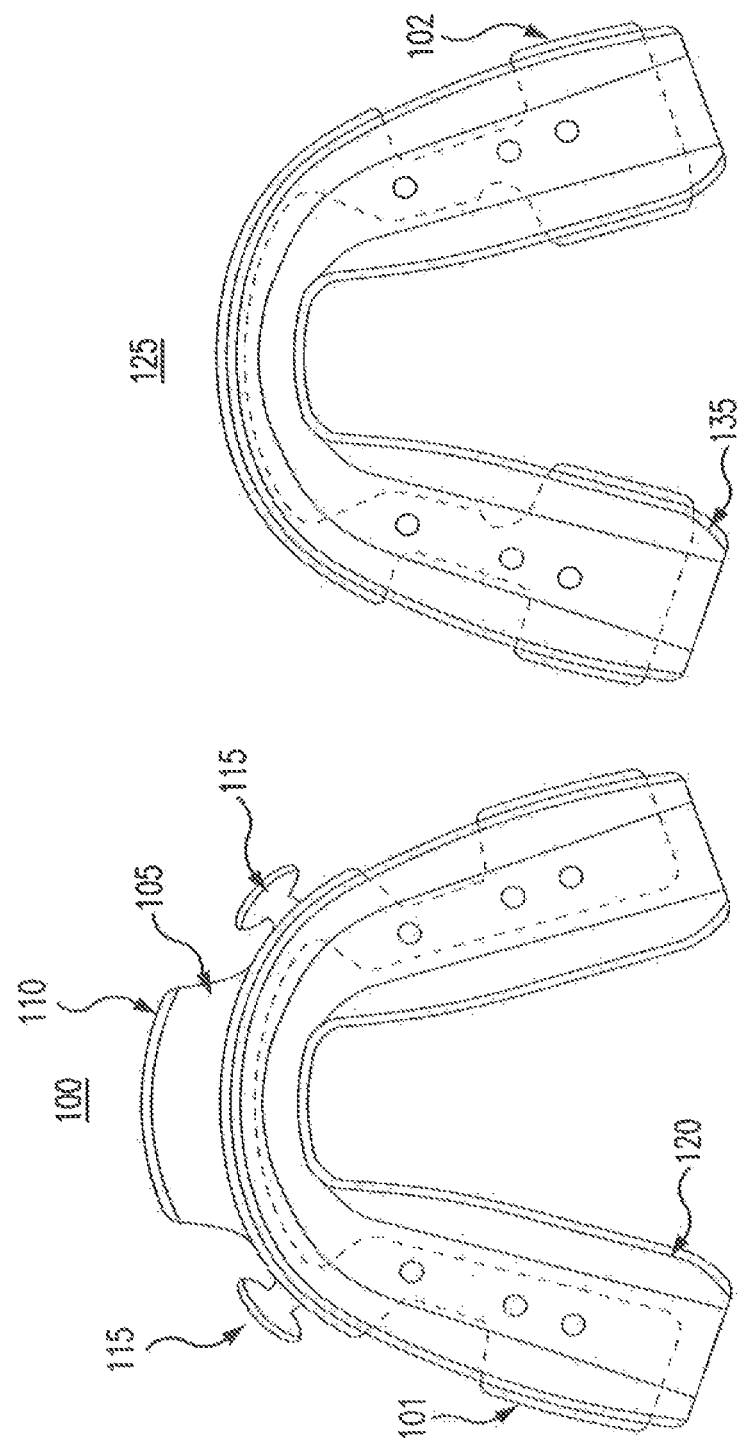
FIG. 1B shows an upper arch and a lower arch.

FIG. 1B shows upper arch 100 and lower arch 125. As provided in FIG. 1B, upper arch 100 may include upper arched frame 101 coupled to upper moldable tray 120. Lower arch 125 may include lower arched frame 102 coupled to lower moldable tray 135. Both upper moldable tray 120 and lower moldable tray 135 may be configured to deform when heated. This deformation may cause upper moldable tray 120 and lower moldable tray 135 to conform to a particular surface, such as the surface of a user's dentition. In this manner, upper moldable tray 120 and lower moldable tray 135 may be configured to receive the upper and lower teeth of a user. In certain embodiments, both upper moldable tray 120 and lower moldable tray 135 may include polycaprolactone.

Figure 1C:
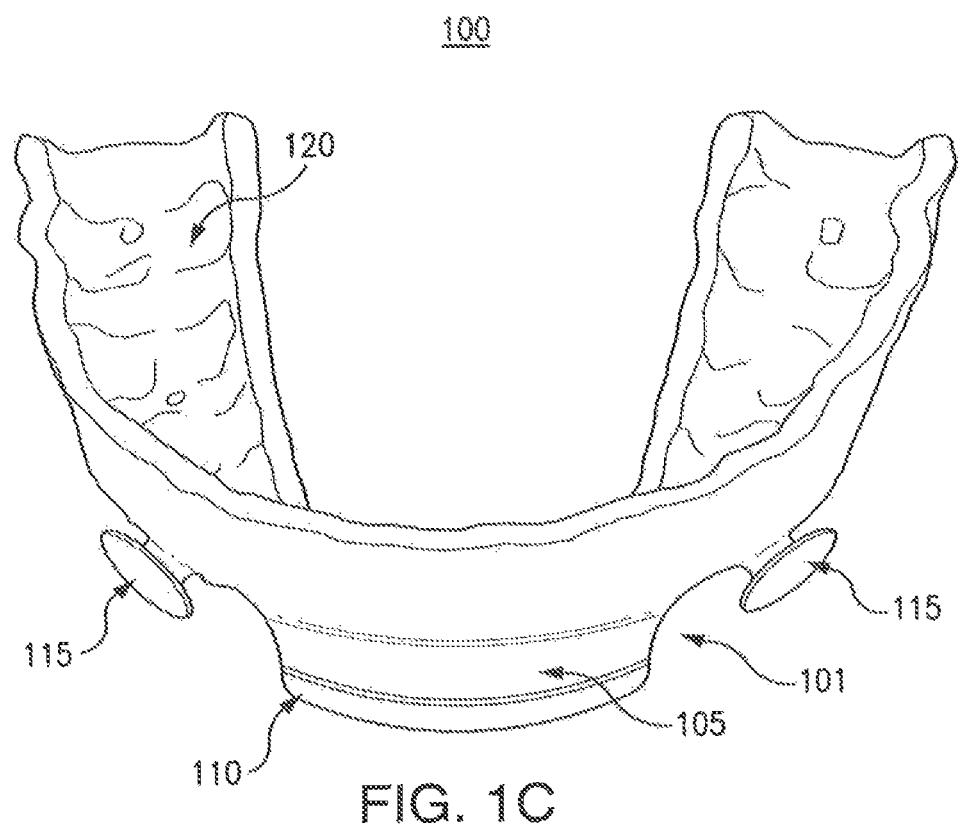
FIGS. 1C-D show an upper arch.
Figure 1D:
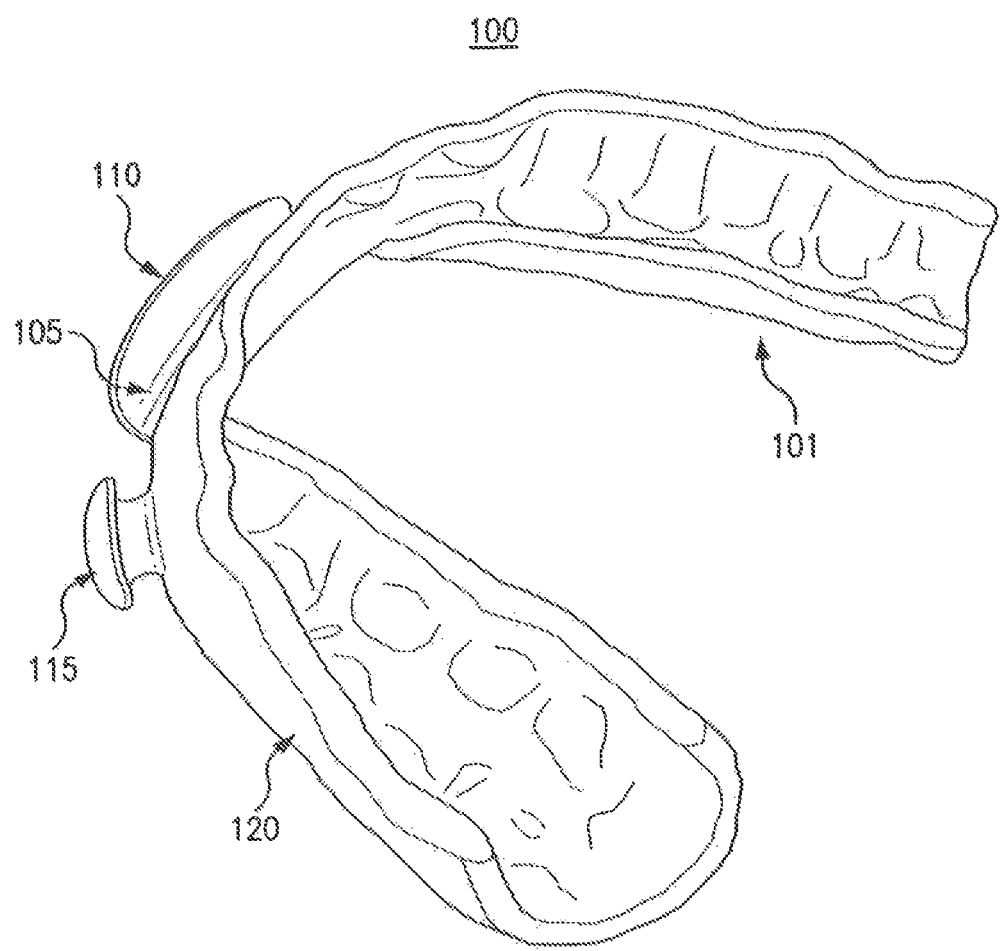

FIGS. 1C and 1D show upper arch 100 of the oral appliance when upper moldable tray 120 has been configured to receive a user's upper dentition. Upper arched frame 101 and moldable tray 120 may form the upper body of upper arch 100. Upper moldable tray 120 may be configured to substantially cover the teeth of a user's maxillary arch. When upper arch 100 is positioned in the user's mouth, upper arch 100 (including upper arched frame 101 and upper moldable tray 120) may be positioned proximate the occlusal surface of the user's maxillary arch. Furthermore, upper arched frame 101 and moldable tray 120 may extend beyond the cuspids of the user's maxillary arch when upper arch 100 is positioned in the user's mouth.

Upper arched frame 101 may include shelf 105. In particular embodiments, shelf 105 may extend in a facial direction from a portion of upper arched frame 101. Shelf 105 may extend across the midline of upper arched frame 101. Shelf 105 may be configured to be positioned proximate to the dental midline of the user's maxillary arch when upper arch 100 is positioned in the user's mouth. Shelf 105 may measure ten to thirty millimeters from one lateral end to another lateral end of shelf 105. Shelf 105 may couple to upper arched frame 101 across the length of shelf 105. In certain embodiments, shelf 105 may allow for lateral movement of a coupler over the length of shelf 105.

Ridge 110 may be coupled to shelf 105 along a facial end of shelf 105. Ridge 110 may extend across the midline of upper arched frame 101. Ridge 110 may be configured to inhibit the disengagement of a coupler. For example, if the coupler is a hook, ridge 110 may provide a surface onto which the hook can hook. In certain embodiments, the positioning of ridge 110 may allow for ridge 110 to be in a user's mouth when upper arch 100 is positioned in the user's mouth. For example, a facial surface ridge 110 may be not more than ten millimeters away from a facial surface of the user's upper central incisor when upper arch 100 is positioned in the user's mouth. In this manner, upper arch 100 may be configured to minimize, eliminate or prevent portions of upper arch 100 from protruding out of the user's mouth when upper arch 100 is positioned in the user's mouth.

Attachment points 115 may be configured to engage a seal that inhibits breathing through the user's mouth when upper arch 100 and the seal are positioned in the user's mouth. As illustrated in FIGS. IC and ID, upper arch 100 may include two attachment points 115 positioned with respect to each other on opposite sides of a plane substantially bisecting upper arch 100. This disclosure contemplates upper arch 100 including any appropriate number of attachment points 115. For example, upper arch 100 may include only one attachment point 115 positioned at the midline of upper arch 100. In certain embodiments, attachment points 115 may be tabs extending from upper arch 100.

Figure 1E:
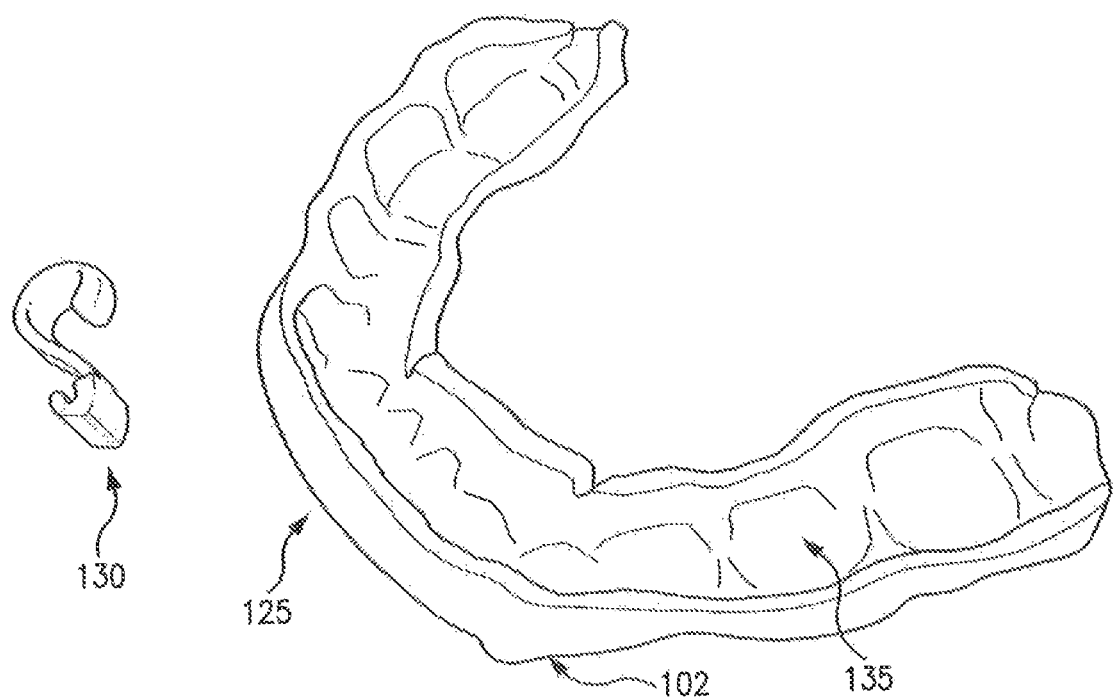
FIGS. 1E-F show a lower arch and a coupler.
Figure 1F:
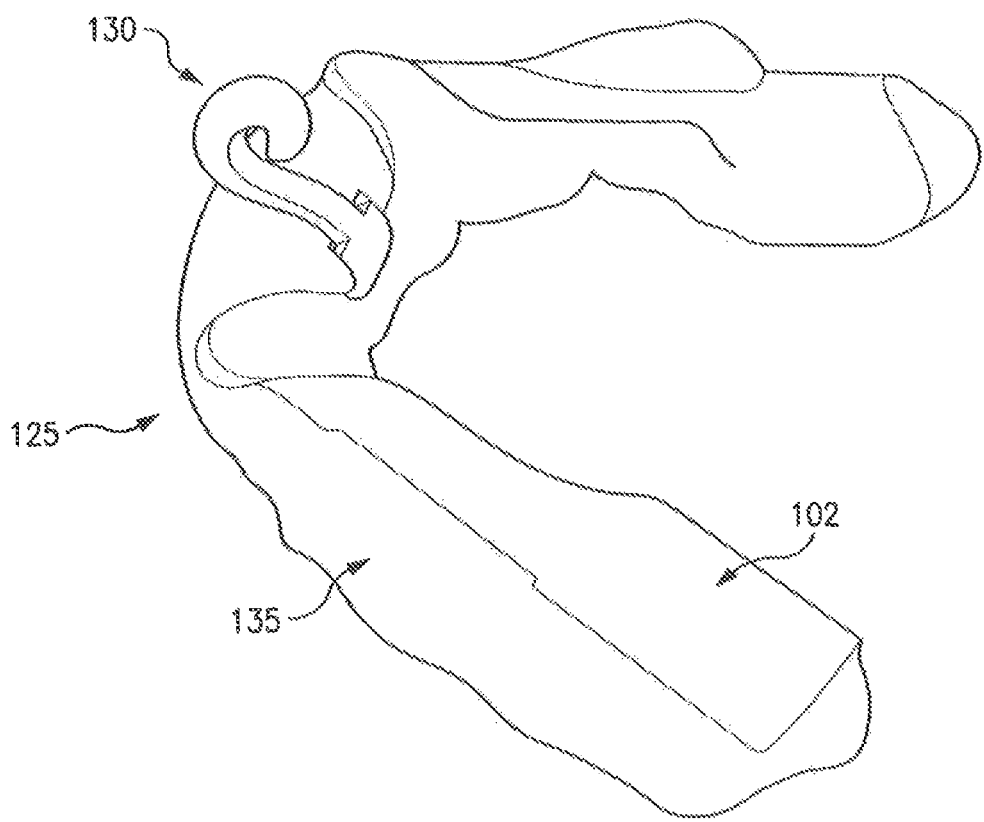

FIGS. 1E and 1F illustrate a lower arch 125 of the oral appliance when lower moldable tray 135 has been configured to receive a user's lower teeth. Lower arch 125 may include a lower arched frame 102 and lower moldable tray 135. FIGS. 1E and 1F also illustrate a coupler 130.

Lower arch 125 may be configured to be positioned proximate the user's mandibular arch when lower arch 125 is positioned in the user's mouth. Lower arched frame 102 and lower moldable tray 135 may be configured to be positioned proximate the occlusal surface of the user's mandibular arch when lower arch 125 is positioned in the user's mouth. Lower arched frame 102 and lower moldable tray 135 may extend beyond the cuspids of the user's mandibular arch when lower arch 125 is positioned in the user's mouth. In certain embodiments, lower arched frame 102 includes polycarbonate resin thermoplastic and lower moldable tray 135 includes polycaprolactone.

Coupler 130 may be configured to couple to lower arched frame 102. For example, coupler 130 may be configured to couple to a portion of lower arched frame 102 at a point along the midline of lower arched frame 102 as shown in FIG. 1D. Coupler 130 may be further configured to be removable from lower arched frame 102 as illustrated in FIG. 1C. Coupler 130 may be a hook or any appropriate mechanism for engaging upper arch 100.

Coupler 130 may be configured to engage a portion of upper arch 100. For example, coupler 130 may be configured to engage shelf 105 and/or ridge 110 of upper arch 100. In certain embodiments, coupler 130 may engage shelf 105 and/or ridge 110 before upper arch 100 and lower arch 125 are inserted in the user's mouth.

Figure 1G:
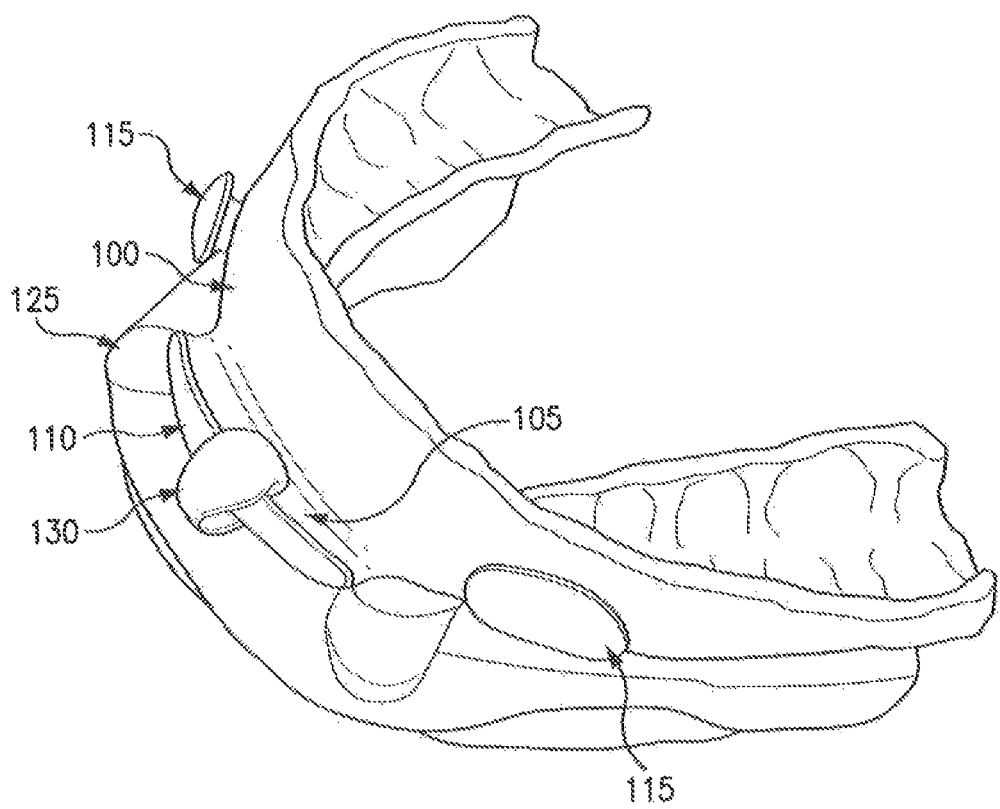
FIG. 1G shows an upper arch, a lower arch, and a coupler.

FIG. 1G shows an upper arch 100, a lower arch 125, and a coupler 130. As provided in FIG. 1G, upper arch 100 may be coupled to lower arch 125 by way of coupler 130. For example, coupler 130 may hook onto shelf 105 and/or ridge 110. Ridge 110 may inhibit coupler 130 from disengaging upper arch 100. When the oral appliance is positioned in the user's mouth, upper arch 100, lower arch 125 and coupler 130 may establish a position of the user's mandibular arch and/or jaw relative to the user's maxillary arch. In this manner, the oral appliance may reduce the user's snoring and/or sleep apnea. Furthermore, as illustrated in FIG. 1G, shelf 105 may allow lower arch 125 to move laterally with respect to upper arch 100 when lower arch 125 is coupled to upper arch 100. In this manner, the user's jaw may continue to move laterally with respect to the user's maxillary arch when the oral appliance is positioned in the user's mouth.

FIGS. 2A through 2E illustrate a seal configured to couple to an oral appliance. The seal may be configured to inhibit the user's breathing through the user's mouth when the oral appliance and seal are positioned in the user's mouth. In this manner, the user may be encouraged to breathe through the nose which may reduce snoring and dryness of the mouth.

Figure 2A:
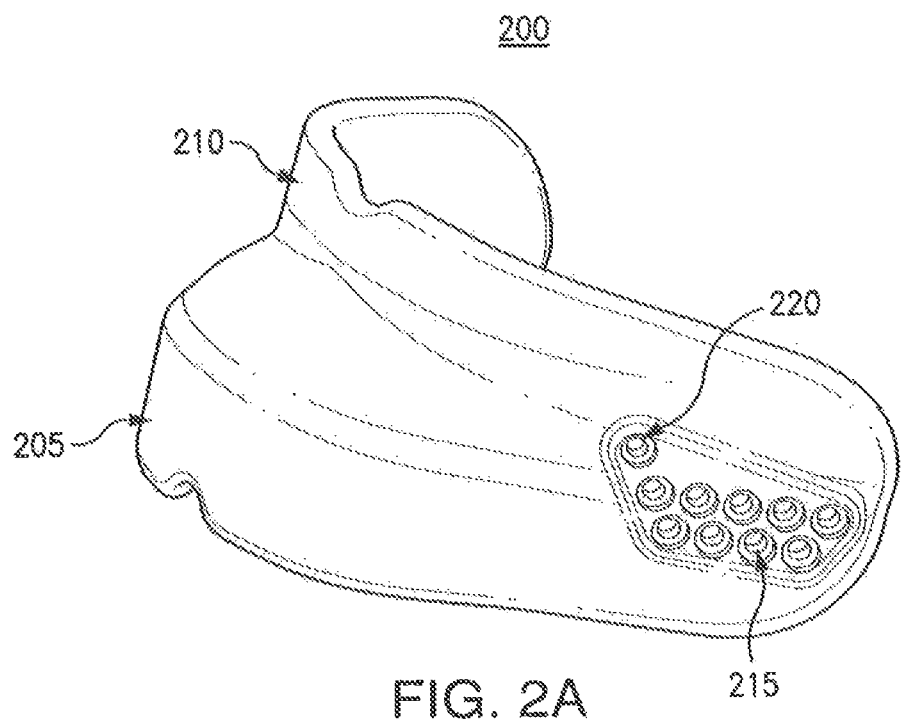
FIGS. 2A-B show a seal.
Figure 2B:
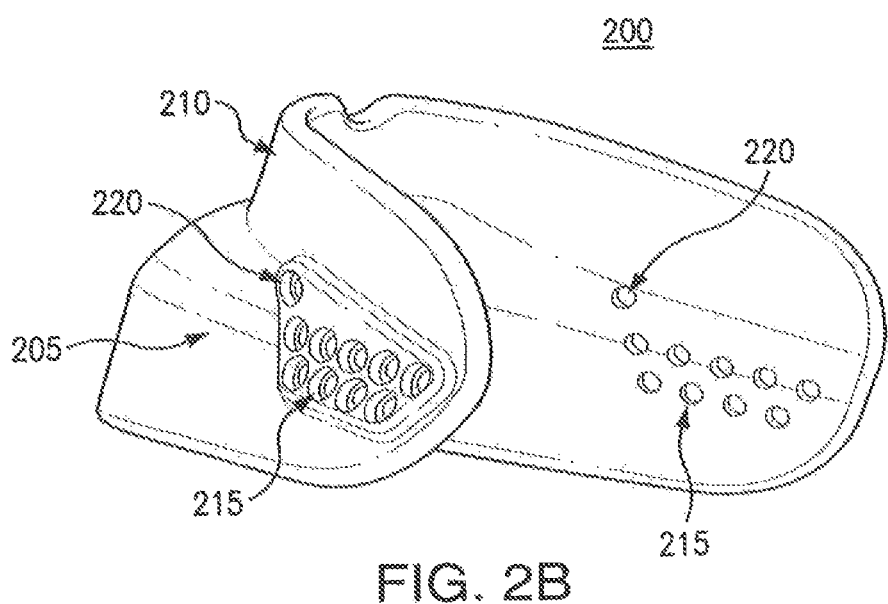

FIGS. 2A and 2B illustrate a seal 200. Seal 200 may include a lower portion 205, an upper portion 210, a lower cavity 215, and an upper cavity 220. Seal 200 may include a flexible material such as silicone rubber. Seal 200 may be configured to attach to an oral appliance. In certain embodiments, seal 200 may attach to the oral appliance by way of lower cavity 215 and upper cavity 220. When seal 200 is attached to the oral appliance and the oral appliance is positioned in the user's mouth, seal 200 may inhibit the user's breathing through the user's mouth. This may encourage the user to breathe through the user's nose while the user is sleeping. This may also reduce dryness of the mouth while the user is sleeping.

In certain embodiments, seal 200 may allow for a lower arch of the oral appliance to move relative to an upper arch of the oral appliance when seal 200 is coupled to the oral appliance. For example, by varying the thickness of the material used to form seal 200, the flexibility of those portions of seal 200 may be increased. By increasing the flexibility of those portions of seal 200, the corresponding portions of the oral appliance may be allowed to move more freely.

Seal 200 may be configured to extend past the cuspids of the user's dentition when seal 200 is positioned in the user's mouth. Seal 200 may further be configured to be positioned in the region between the user's teeth and the user's lips when seal 200 is positioned in the user's mouth. In this manner, seal 200 may be configured to minimize, eliminate or prevent portions of seal 200 from protruding out of the user's mouth when seal 200 is positioned in the user's mouth.

Lower portion 205 may be configured to be positioned proximate the user's mandibular arch when seal 200 is positioned in the user's mouth. Upper portion 210 may be configured to be positioned proximate the user's maxillary arch when seal 200 is positioned in the user's mouth. In certain embodiments, lower portion 205 may be thinner than upper portion 210. In this manner, lower portion 205 may be more flexible than upper portion 210. As a result, a lower arch of an oral appliance coupled to seal 200 may be able to move more freely relative to an upper arch of the oral appliance coupled to seal 200.

Upper cavity 220 may be configured to attach to an upper arch of an oral appliance. For example, upper cavity 220 may be configured to attach to the upper arch. Using the example of FIG. 1A, upper cavity 220 may be configured to attach to an attachment point 115 of upper arch 100. In certain embodiments, attachment point 115 may be a tab. This disclosure contemplates seal 200 including any appropriate number of upper cavities 220 in any appropriate configuration. For example, seal 200 may include only one upper cavity 220 positioned at a point along the midline of seal 200. As another example, and as shown in FIG. 2B, seal 200 may include multiple upper cavities 220 on opposite sides of seal 200.

Seal 200 may include a plurality of lower cavities 215. Each lower cavity 215 may be configured to couple to a lower arch of the oral appliance. For example, each lower cavity 215 may be configured to engage a tab extending from the lower arch. Seal 200 may have lower cavities 215 and corresponding lower cavities 215 on opposite sides of seal 200 as illustrated in FIG. 2B.

By engaging the lower arch to various lower cavities 215, the positioning of the lower arch relative to the upper arch may be adjusted. By adjusting this position, the tensile force exerted on the lower arch relative to the upper arch may be adjusted. For example, coupling the lower arch to a first set of lower cavities 215 may result in the lower arch being pulled more forward relative to the upper arch than if the lower arch coupled to a second set of lower cavities 215. In this manner, the positioning of the user's mandibular arch relative to the user's maxillary arch may be adjusted when the oral appliance is positioned in the user's mouth.

Figure 2C:
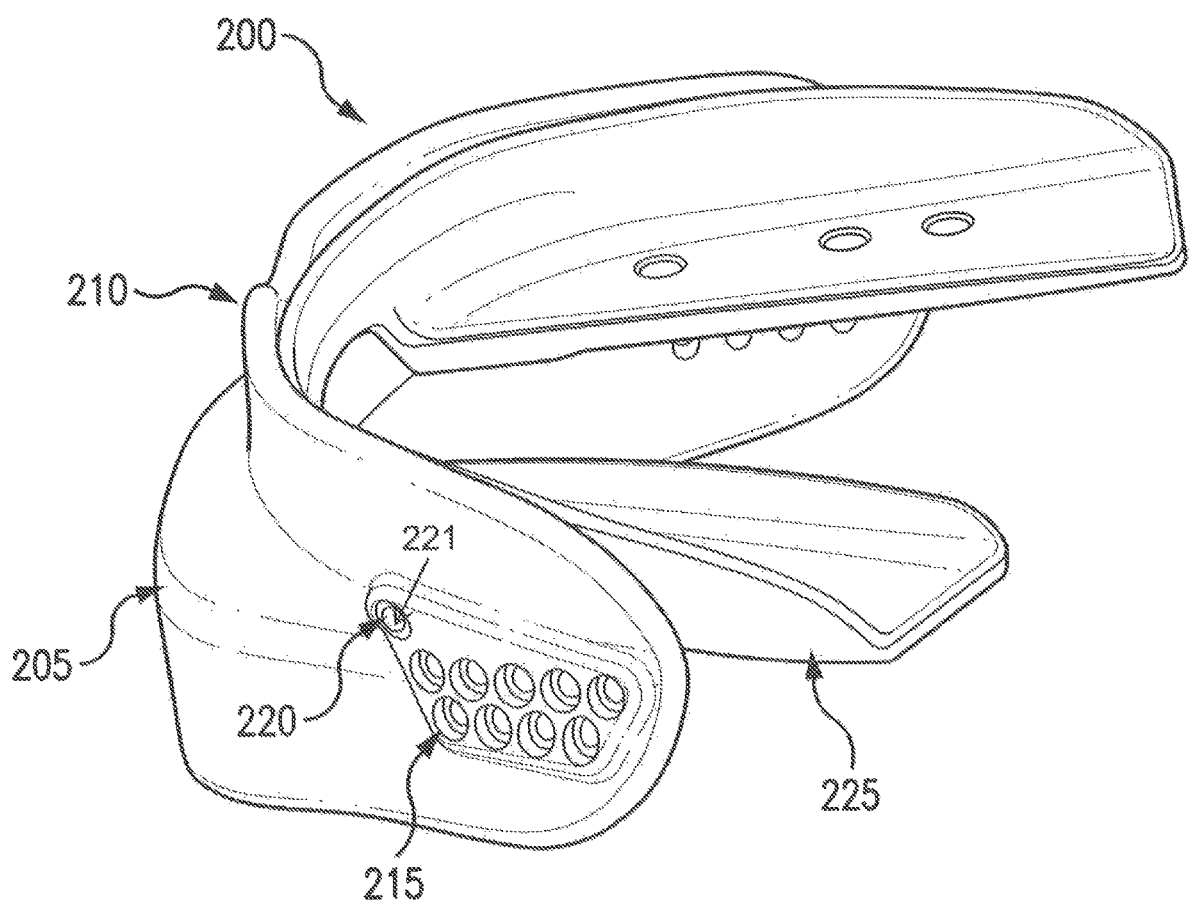
FIG. 2C shows a seal coupled to an upper arch.

FIG. 2C shows seal 200 coupled to an upper arched frame 225. As provided in FIG. 2C, upper arched frame 225 may couple to seal 200 via upper cavity 220. As shown, upper arched frame 225 may include a tab 221 that is configured to engage upper cavity 220.

Figure 2D:
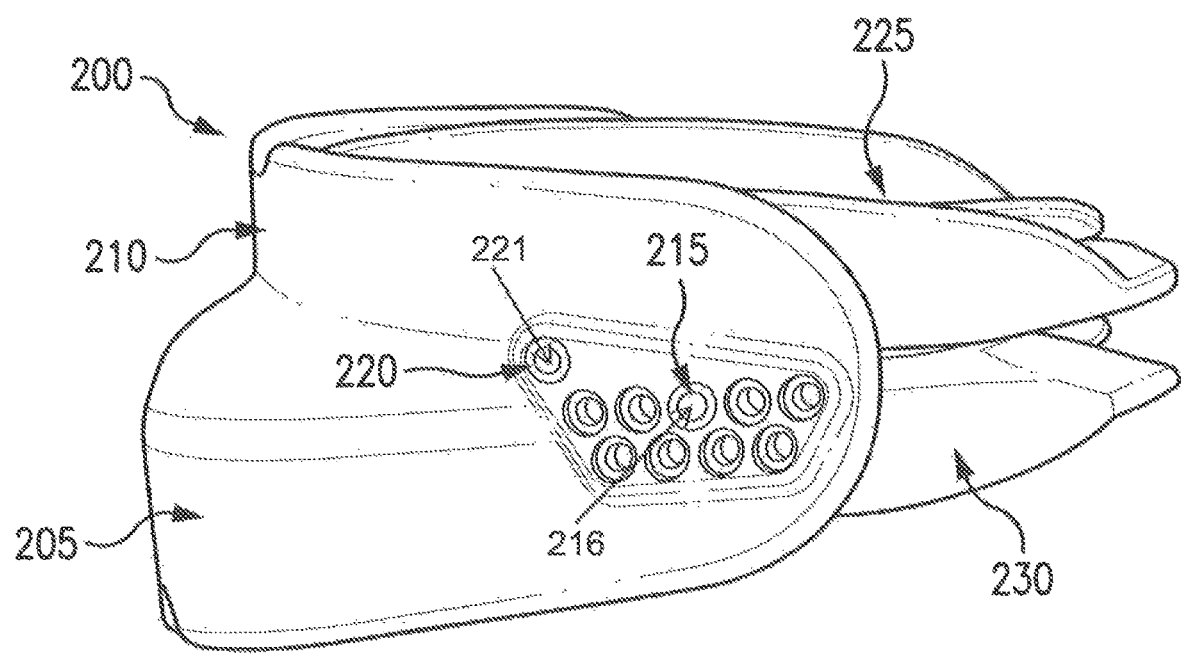
FIG. 2D shows a seal coupled to an upper arch and a lower arch.

FIG. 2D illustrates seal 200 coupled to upper arched frame 225 and lower arched frame 230. As illustrated in FIG. 2D, lower arched frame 230 may couple to seal 200 through lower cavity 215. Lower arched frame 230 may include a tab 216 that is configured to engage lower cavity 215. As shown in FIG. 2D, the position of lower arched frame 230 relative to upper arched frame 225 may be adjusted by coupling lower arched frame 238 through another lower cavity 215. In this manner, the tensile three exerted on lower arched frame 230 relative to upper arched frame 225 may be adjusted.

This disclosure contemplates upper arched frame 225 coupling to seal 200 through any appropriate number of upper cavities 220. For example, upper arched frame 225 may couple to seal 200 through an upper cavity 220 positioned at a point along the midline of seal 200. A tab 221 of upper arched frame 225 may be configured to engage upper cavity 220 at the point along the midline.

Figure 2E:
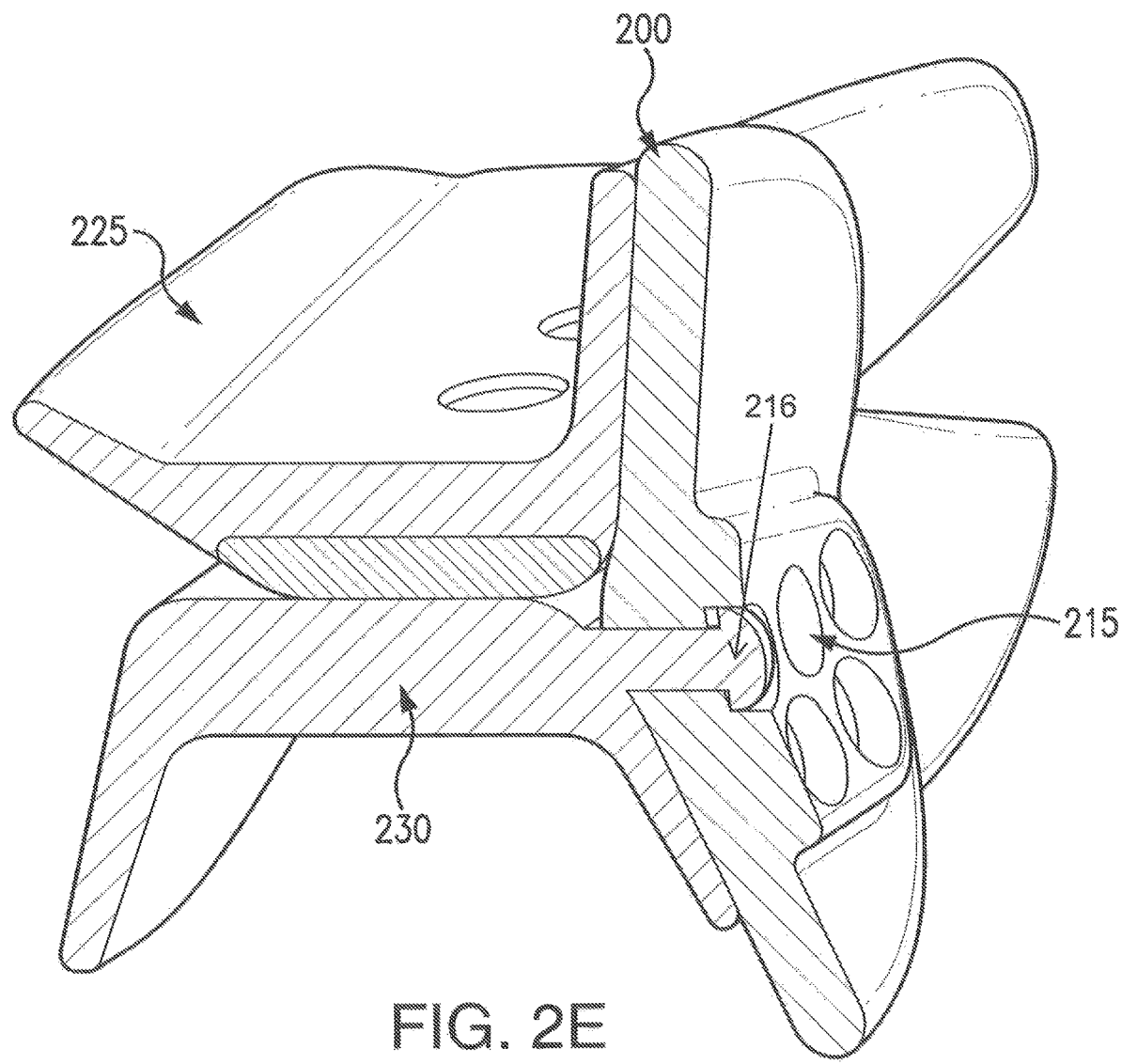
FIG. 2E shows a cross section of a seal coupled to an upper arch and a lower arch.

FIG. 2E shows a cross section of seal 200 coupled to upper arched frame 225 and lower arched frame 230. As illustrated in FIG. 2E, a tab 216 of lower arched frame 230 may be configured to engage a lower cavity 215 of seal 200. Although this disclosure describes an oral appliance including tabs that couple to seal 200, this disclosure contemplates the oral appliance including any appropriate mechanism to couple to seal 200.

In certain embodiments, seal 200 may be coupled to an oral appliance by way of a deformable material such as an adhesive, a glue, or a gel. The oral appliance may be first positioned in a user's mouth. Then the deformable material, such as a glue, may be applied to one or more of the oral appliance and/or the seal. The seal may then be pressed onto the oral appliance and the glue may couple the seal to the oral appliance. In this manner, the seal may be used with an oral appliance that is not configured to couple to the seal through upper cavities and lower cavities.

Figure 3A:
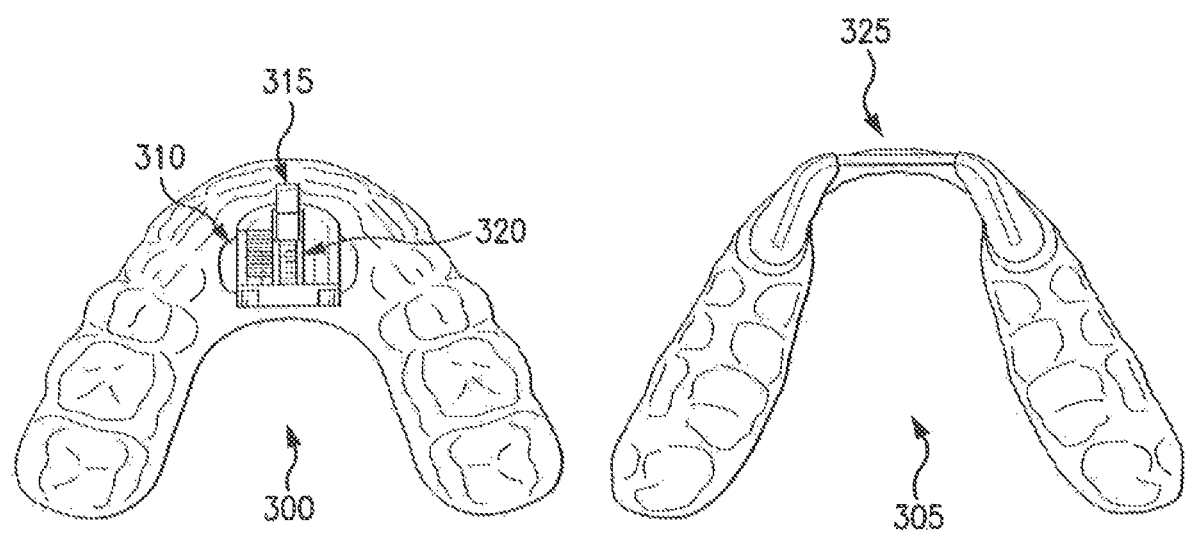
FIG. 3A shows an oral appliance that includes an upper arched frame and a lower arched frame.

FIG. 3A shows an oral appliance that includes a lower arch 300 and an upper arch 305. Lower arch 300 includes an adjustment mechanism 310, and upper arch 305 includes a receiving mechanism 325. Adjustment mechanism 310 includes a hook 315 and a threaded adjustor 320.

Lower arch 300 is configured to be positioned proximate to the occlusal surface of a user's mandibular (lower) arch such that lower arch 300 extends beyond the lower cuspids of the user's mandibular arch when lower arch 300 is positioned in the user's mouth. Lower arch 300 may cover a plurality of the teeth of the user's mandibular arch. Furthermore, a midline of lower arch 300 may align substantially with the anterior midline of the user's mouth when lower arch 300 is positioned in the user's mouth. Lower arch 300 may include polycarbonate and/or any other suitable material. For example, lower arch 300 may include thermoplastic polyurethane, acrylic, and/or polyethylene terephthalate.

Upper arch 305 is configured to be positioned proximate to the occlusal surface of a user's maxillary (upper) arch such that upper arch 305 extends beyond the upper cuspids of the user's maxillary arch when upper arch 305 is positioned in the user's mouth. Upper arch 305 may cover a plurality of the teeth of the user's maxillary arch. Furthermore, a midline of upper arch 305 may align substantially with the anterior midline of the user's mouth when upper arch 305 is positioned in the user's mouth. Upper arch 305 may include polycarbonate resin thermoplastic or any other suitable material. For example, upper arch 305 may include thermoplastic polyurethane, acrylic, and/or polyethylene terephthalate.

In particular embodiments, adjustment mechanism 310 and receiving mechanism 325 are configured to engage each other to adjust the forward position of lower arch 300 relative to upper arch 305. When lower arch 300 and upper arch 305 are positioned in a user's mouth, adjustment mechanism 310 and receiving mechanism 325 may adjust the forward position of the mandibular arch relative to the maxillary arch. Although this disclosure shows adjustment mechanism 310 adjusting the forward position of lower arch 300 using hook 315 and threaded adjustor 320, this disclosure contemplates adjustment mechanism 310 adjusting the forward position of lower arch 300 using any number of appropriate mechanisms.

Hook 315 is configured to engage receiving mechanism 325. Threaded adjustor 320 may be used to adjust the forward position of hook 315 relative to lower arch 300. For example, threaded adjustor may be turned to move hook 315 closer to the back or front of the user's mouth when lower arch 300 is positioned in the user's mouth. When lower arch 300 and upper arch 305 are positioned in the user's mouth and when hook 315 is engaged with receiving mechanism 325, threaded adjustor 320 may be used to adjust the forward position of lower arch 300 relative to upper arch 305. For example, threaded adjustor may be turned so that hook 315 and receiving mechanism 325 pull lower arch 300 towards the front of the user's mouth or push lower arch 300 towards the back of the user's mouth. In this manner, the forward position of the user's jaw may be adjusted to open or close the user's breathing passageway.

Hook 315 and receiving mechanism 325 are configured to move laterally with respect to each other when hook 315 is engaged with receiving mechanism 325. This allows the user's lower jaw to retain lateral movement (left to right) when lower arch 300 and upper arch 305 are positioned in the user's mouth and when hook 315 is engaged with receiving mechanism 325.

In particular embodiments, the shape and configuration of receiving mechanism 325 may provide space behind a user's upper incisors when upper arch 305 is positioned in the user's mouth. The user may then rest his tongue in that space, which corresponds to the natural resting position of the user's tongue. Furthermore, the shape and configuration of receiving mechanism 325 may improve structural support for upper arch 305 in particular embodiments.

Figure 3B:
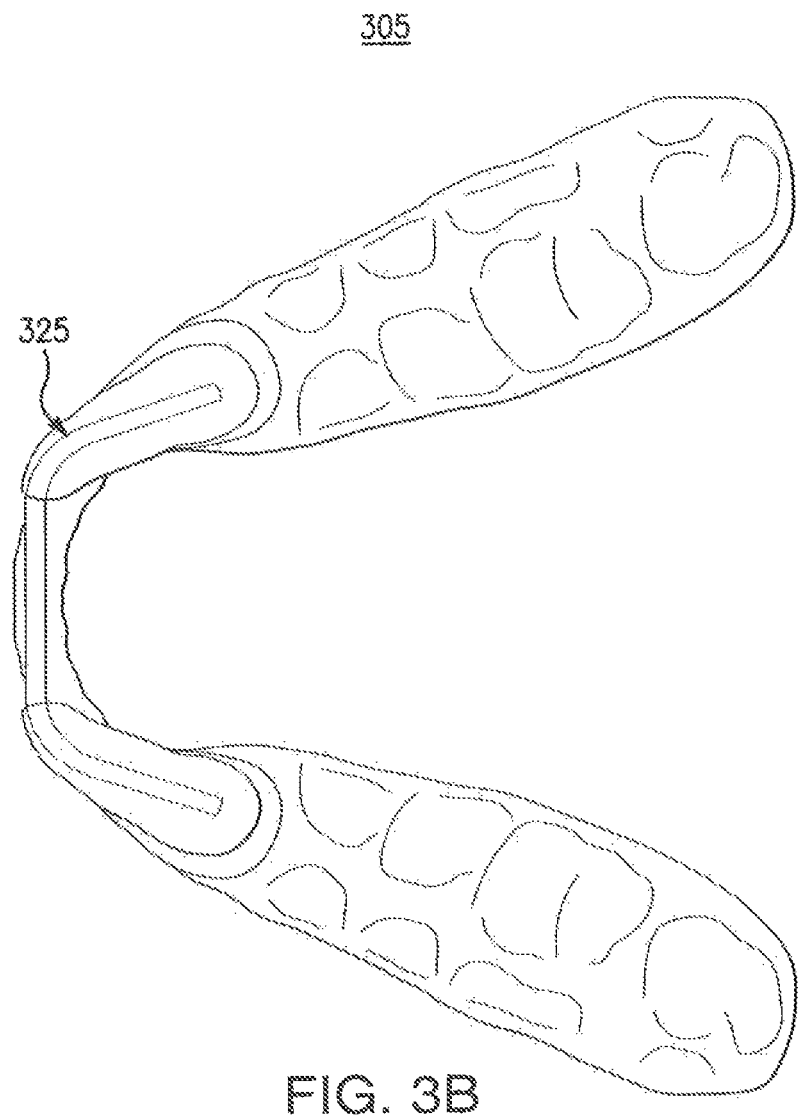
FIGS. 3B-C show a lower arched frame.
Figure 3C:
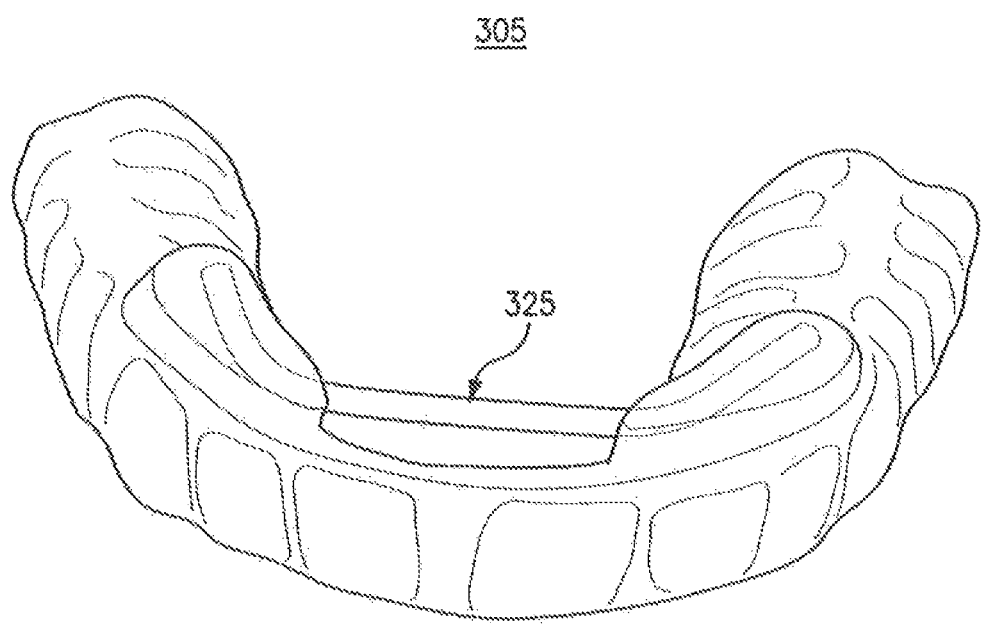

FIGS. 3B and 3C show different perspectives of upper arch 305. As shown, the shape and configuration of receiving mechanism 325 provide a space behind a user's upper incisors in which the user's tongue can rest when upper arch 305 is positioned in the user's mouth. With this configuration, upper arch 305 does not interfere with the position of the user's tongue against the palate. Furthermore, the shape and configuration of receiving mechanism 325 improves structural support for upper arch 305.

Figure 3D:
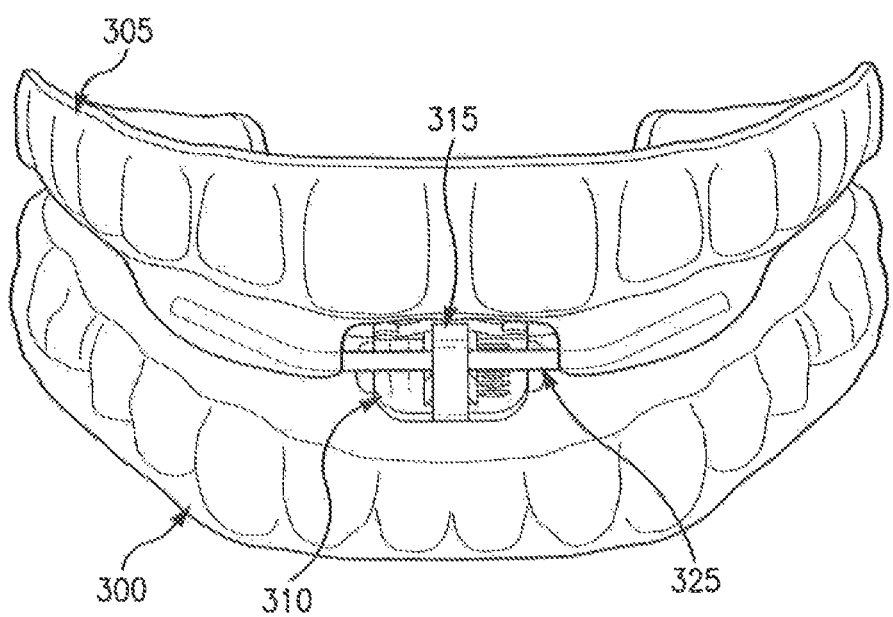
FIGS. 3D-F show an oral appliance that includes an upper arched frame and a lower arched frame.
Figure 3E:
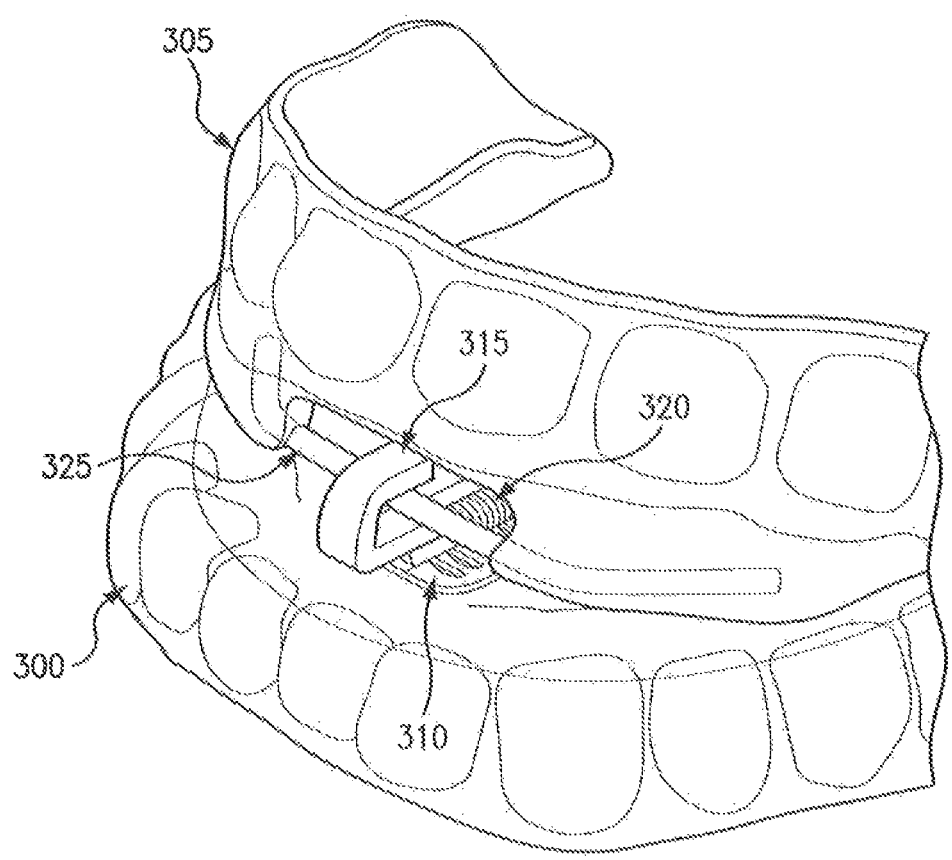
Figure 3F:
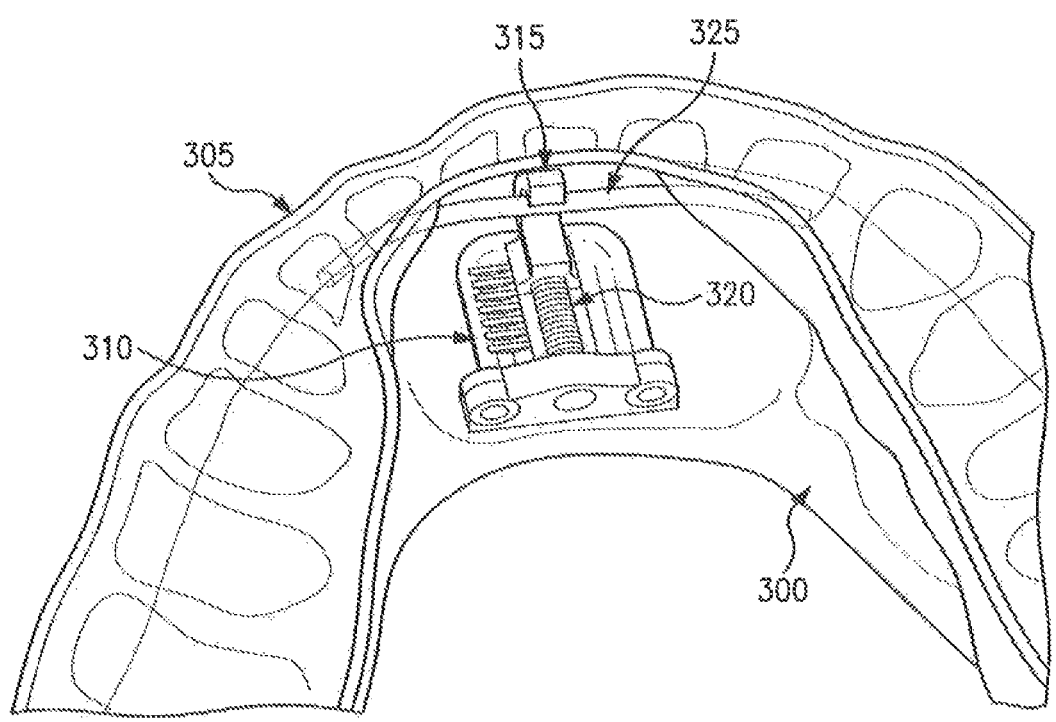
Figure 4A:
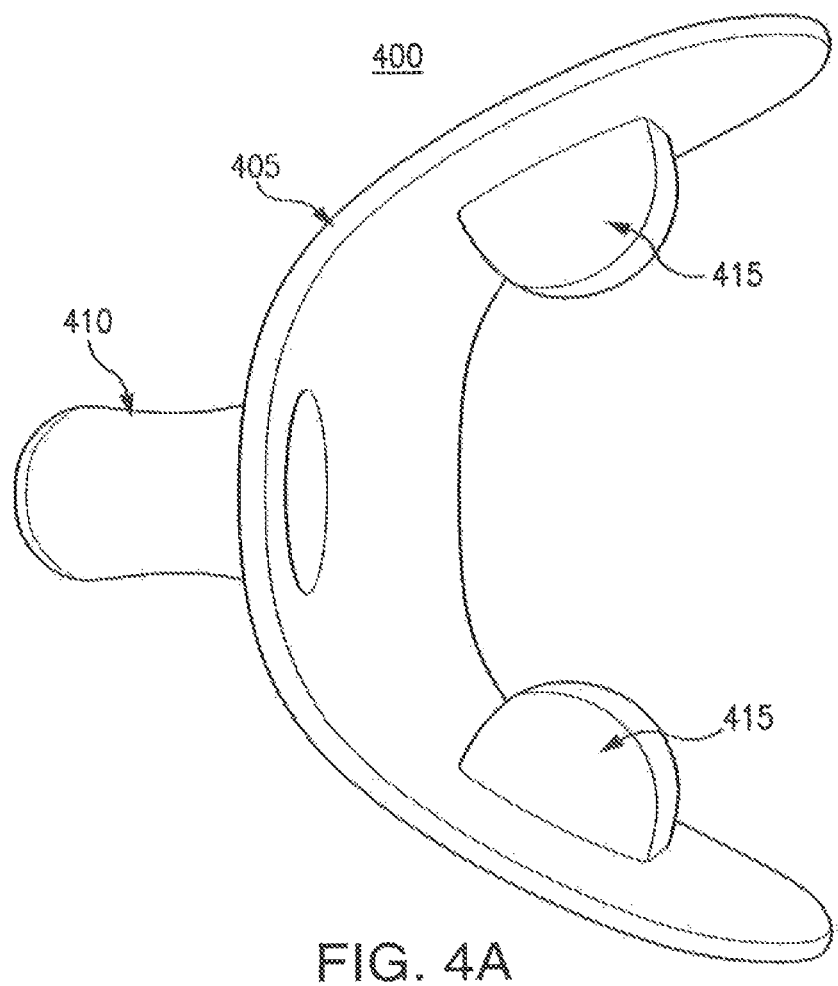
FIGS. 4A-C show a seal.
Figure 4B:
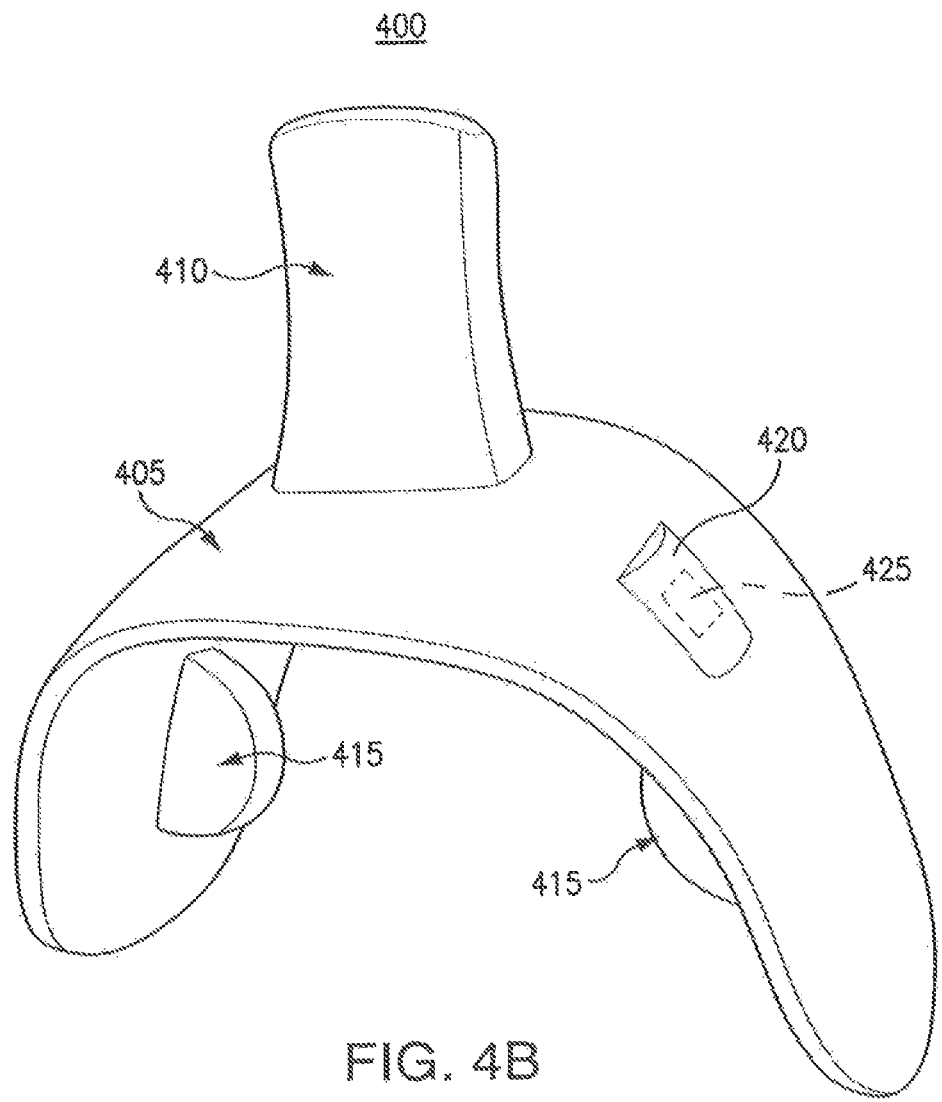
Figure 4C:
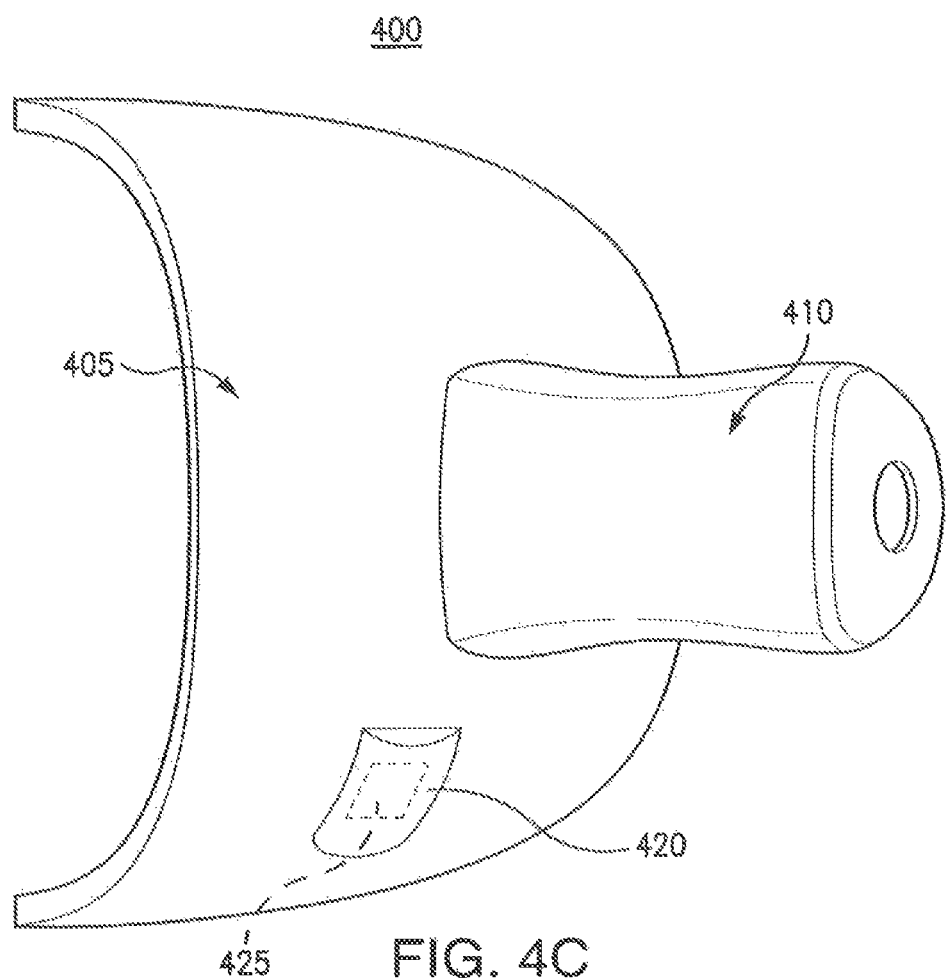
Figure 5A:
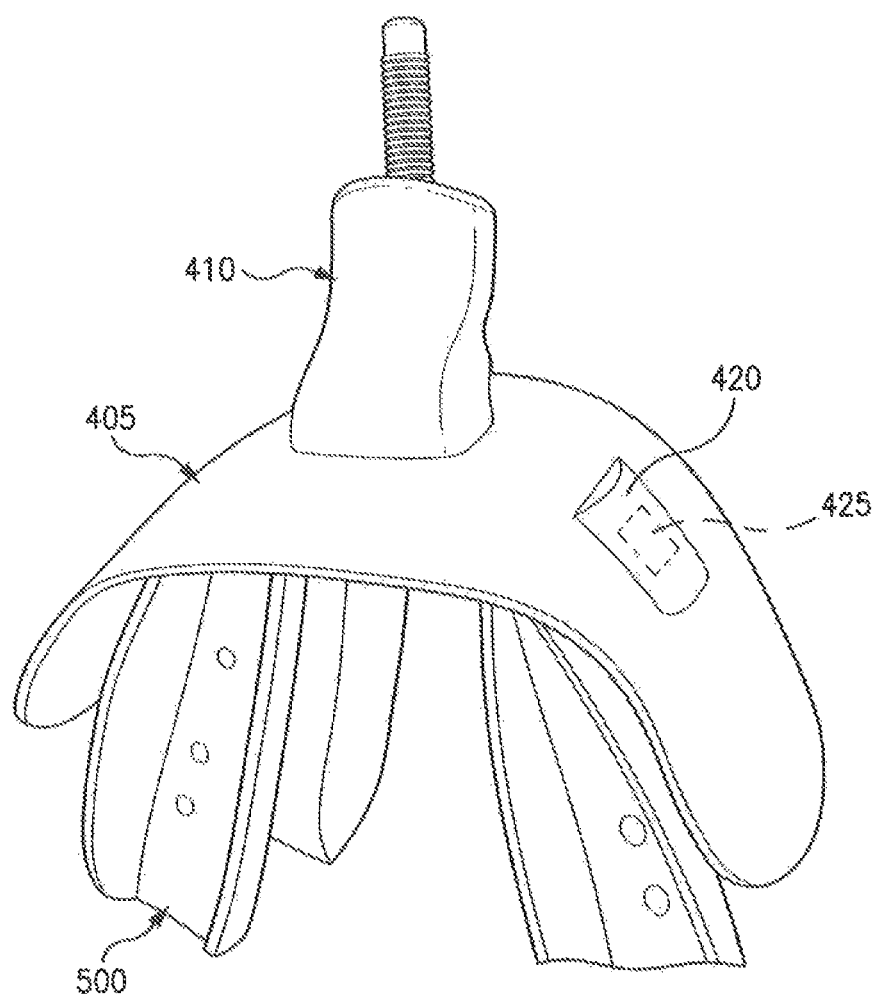
FIGS. 5A-D show a seal and an oral appliance.
Figure 5B:
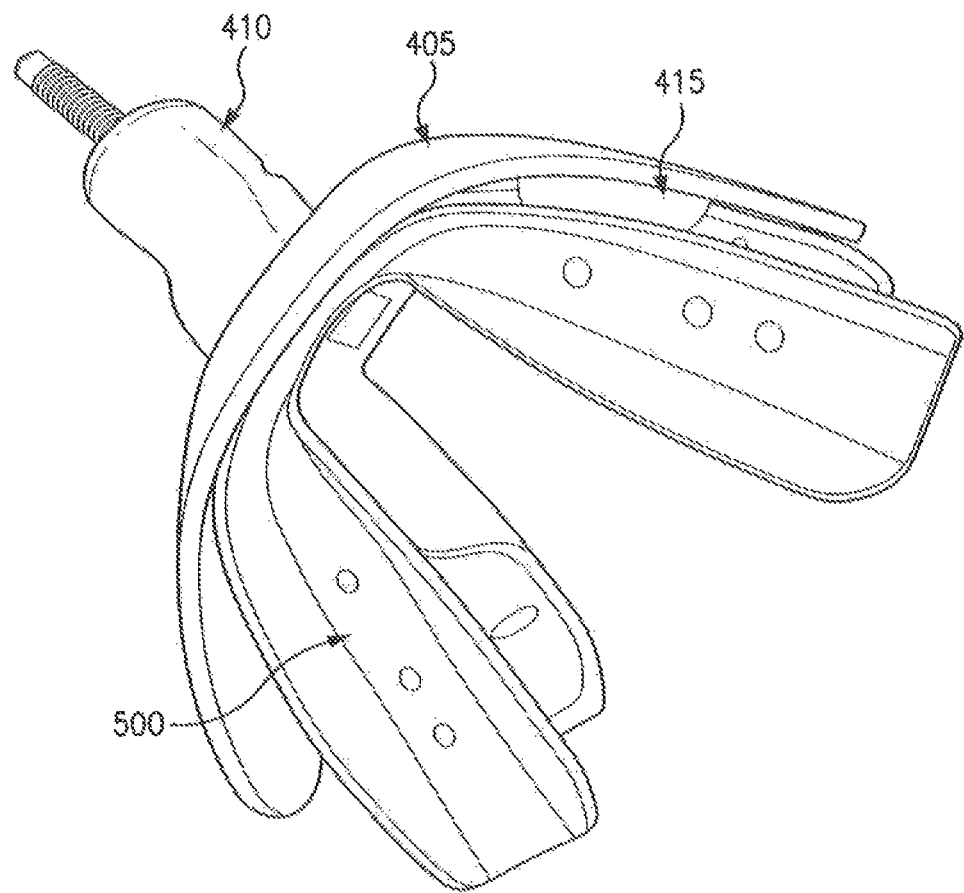
Figure 5C:
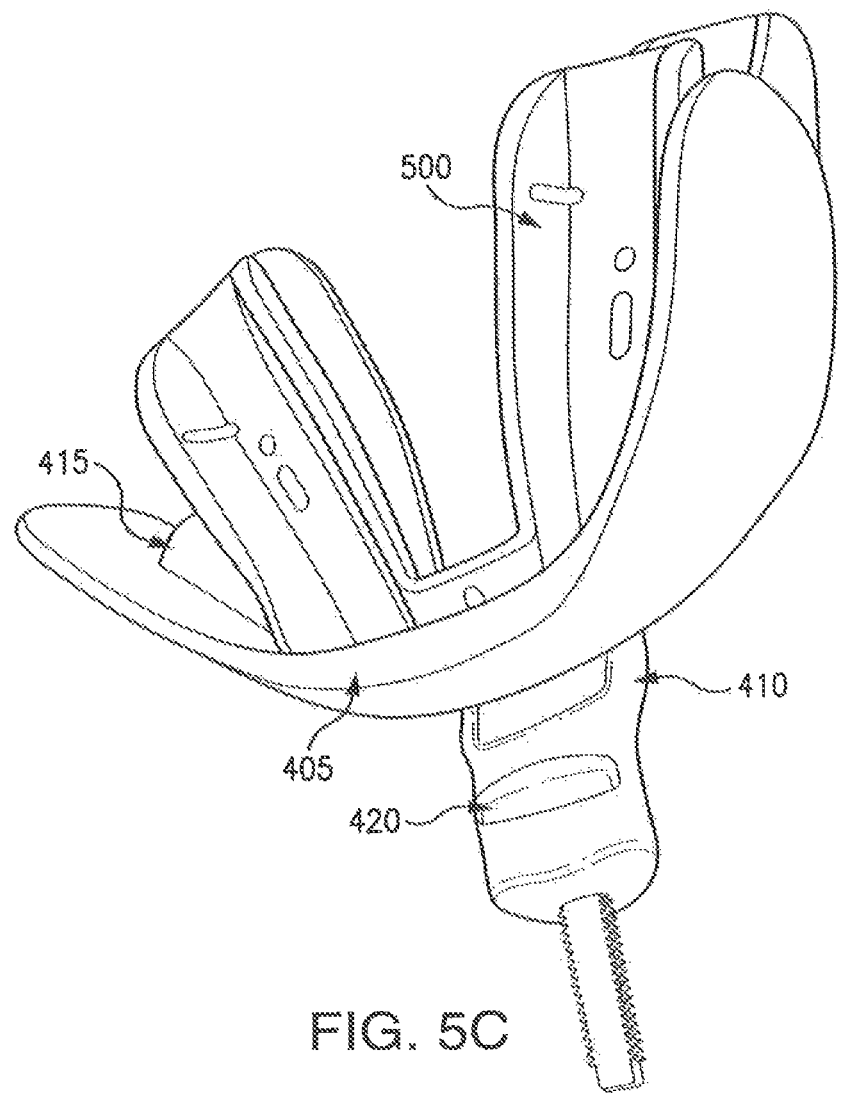
Figure 5D:
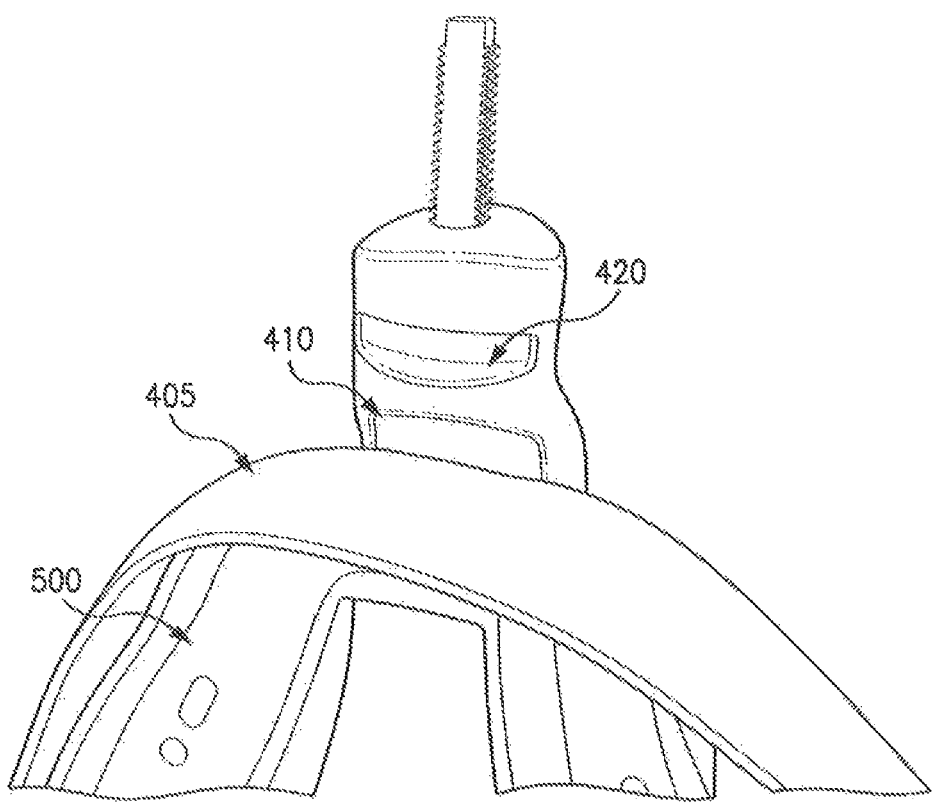

FIGS. 3D-3F show different perspectives of lower arch 300 and upper arch 305 when hook 315 is engaged with receiving mechanism 325. As shown, hook 315 is configured to engage with receiving mechanism 325. Hook 315 may move laterally when engaged with receiving mechanism 325. Threaded adjustor 120 may be used to adjust the forward position of hook 315 and lower arch 300 relative to upper arch 305.

This disclosure contemplates an oral appliance where lower arch 300 and upper arch 305 are coupled so that their relative positions are not adjustable. In this manner, the forward position of lower arch 300 may be fixed relative to the forward position of upper arch 305.

FIGS. 4A-5D show different perspectives of seal 400. As shown, seal 400 includes an arched body 405, receiving mechanism 410, pads 415, and ridge 420. Seal 400 may be configured to engage an oral appliance 500, as shown in FIGS. 5A-5D. This disclosure contemplates seal 400 being made of a flexible material such as, for example, liquid silicon rubber or any other appropriate material, such as for example, shore A 40 hardness SLR, or similar rubber material, such as Santoprene.

Arched body 405 may be configured to rest in a user's oral vestibule (e.g., the region of the user's mouth between the user's dentition and the user's lips) and to cover substantially the user's mouth when oral appliance 500 is positioned in the user's mouth. Arched body 405 may be configured to extend beyond the cuspids of the user's maxillary dentition when seal 400 and/or oral appliance 500 is positioned in the user's mouth. In particular embodiments, by substantially covering a user's mouth, arched body 405 inhibits the flow of air through the user's mouth. In this manner, arched body 405 may prevent drooling and mouth dryness by encouraging the user to breathe through the user's nose when the user is sleeping. For clarity, this disclosure will describe arched body 405 as resting in the user's mouth, however, this disclosure also contemplates arched body 405 resting external to the user's oral vestibule.

In certain embodiments, the thickness of arched body 405 may not be uniform. As an example, a portion of arched body 405 may be thinner at an end closer to the user's mandibular arch than a portion at an end closer to the user's maxillary arch. In this manner, arched body 405 may allow for movement of the user's mandibular arch when oral appliance 500 is positioned in the user's mouth.

Receiving mechanism 410 may be coupled to arched body 405. Receiving mechanism 410 may be configured to engage oral appliance 500. In particular embodiments, receiving mechanism includes a tube that engages oral appliance 500. The tube is configured so that a post of oral appliance 500 may go through the tube. In particular embodiments, the tube includes ridge 420 that engages oral appliance 500. Ridge 420 may be located on the inside of the tube. When the post of oral appliance 500 is positioned into the tube, ridge 420 may engage a portion of oral appliance 500 such that the position of seal 400 is fixed relative to the position of oral appliance 500.

Receiving mechanism 410 may include a thin section on one side that may compress and/or fold as oral appliance 500 moves forward. This allows for the end of receiving mechanism 410 to remain stationary relative to oral appliance 500, which allows seal 400 to stay in contact with the upper and/or lower trays of oral appliance 500. The thin section may be from 0.4 mm thick to 2.0 mm thick.

In certain embodiments, receiving mechanism 410 includes a post that engages oral appliance 500. The post may engage the arched frames of oral appliance 500 so that the relative position of seal 400 is fixed relative to the position of oral appliance 500. In certain embodiments, seal 400 does not include receiving mechanism 410. In other embodiments, receiving mechanism 410 extends towards the inside of the user's mouth when seal 400 is positioned in the user's mouth.

Pad 415 may be coupled to arched body 405. In particular embodiments, pad 415 may separate the arched frames of oral appliance 500 when seal 400 is engaged with oral appliance 500. In this manner, pad 415 may increase the vertical space in the oral cavity when oral appliance 500 is positioned in the user's mouth, which may reduce the amount of protrusion of the user's mandible. Pad 415 may also help prevent the user from clenching the user's jaw. Furthermore, pad 415 may help the arched frames of oral appliance 500 maintain their relative positions. Pad 415 may be molded integrally, or may be assembled. Pad 415 may be of a thickness ranging from 1 mm to 12 mm. In particular embodiments, seal 400 may be molded and supplied with different integral pads 415. In certain embodiments, pad 415 may clip onto seal 400. These pads 415 may include any appropriate material. For example, pads 415 may include SLR or harder thermoplastics such as nylon or polycarbonate. As another example, pads 415 may include a compressible and resilient material that cushions the point of contact between the arched frames of oral appliance 500. This disclosure contemplates seal 400 including any appropriate number of pads 415 coupled to arched body 405 in any appropriate manner.

Similar to previous embodiments, oral appliance 500 may include an upper arch and a lower arch. The upper arch may include an upper arched frame and the lower arch may include a lower arched frame. The upper arched frame may be configured to be positioned proximate a user's maxillary dentition when the upper arch is positioned in the user's mouth. The lower arched frame may be configured to be positioned proximate the user's mandibular dentition when the lower arch is positioned in the user's mouth. The upper arch and the lower arch may include polycarbonate or any similar rigid or semi-rigid thermoplastic that can withstand deforming and/or melting at 100 degrees Celsius, such as for example polycarbonate resin thermoplastic and/or nylon.

In certain embodiments, the upper arch and the lower arch of oral appliance 500 may be coupled to moldable trays. Each moldable tray may be configured to receive a portion of the user's dentition when oral appliance 500 is positioned in the user's mouth. For example, an upper moldable tray may be configured to receive a portion of the user's maxillary dentition and a lower moldable tray may be configured to receive a portion of the user's mandibular dentition. Each moldable tray may include polycaprolactone.

Seal 400 may include a receptacle 420 and an electronic compliance monitor 425. Receptacle 420 may be any appropriate structure for holding electronic compliance monitor 425, such as for example, a pocket or a sleeve. This disclosure also contemplates electronic compliance monitor 425 being molded in to seal 400 using silicon rubber. For example, a quickform silicon may be applied over a surface of the electronic compliance monitor 425 to enclose electronic compliance monitor 425 and to attach electronic compliance monitor 425 to seal 400.

Electronic compliance monitor 425 may monitor certain features of the environment around electronic compliance monitor 425, such as for example, temperature, air flow, movement, pulse, blood oxygen levels (such as for example through pulse oximetry), etc. In certain embodiments, electronic compliance monitor 425 may include a chip and/or sensors that measures such features and logs the measurements for further analysis. These measurements may be used, for example, to determine if seal 400 and/or oral appliance 500 are positioned properly in the user's mouth or if they are being used appropriately. An example of electronic compliance monitor 425 includes the DentiTrac® product.

Electronic compliance monitor 425 communicates measurements to a device for real-time monitoring. For example, electronic compliance monitor 425 may communicate measurements to a device, such as a mobile phone, over Bluetooth. A doctor and a user may then monitor the measurements when seal 400 and electronic compliance monitor 425 are positioned in the user's mouth. Adjustments may then be made to seal 400 based on the observed measurements.

In certain embodiments, electronic compliance monitor 425 is removable from receptacle 420 without altering the structure of seal 425. In this manner, seal 400 may be manufactured without electronic compliance monitor 425, which reduces the cost of electronic compliance monitor 425. It may not be desirable to mold electronic compliance monitor 425 into seal 400 in some embodiments because electronic monitoring may not be performed at all times when seal 400 is positioned in the user's mouth. As a result, a user need not unnecessarily position electronic compliance monitor 425 in the user's mouth.

This disclosure contemplates electronic compliance monitor 425 being used with any appropriate oral appliance, and not merely with seal 400. For example, electronic compliance monitor 425 may be coupled to seal 200. As another example, any of upper arch 100, lower arch 125, lower arch 300, upper arch 305, oral appliance 500, and oral appliance 600 may be configured to couple to electronic compliance monitor 425. This disclosure contemplates using any appropriate mechanism to couple electronic compliance monitor 425 to any of the devices disclosed herein. For example, a sleeve may be fitted over a portion (such as a post) of oral appliance 500 and/or oral appliance 600 and electronic compliance monitor 425 may be coupled to the sleeve.

FIGS. 6A-66B show different perspectives of an oral appliance 600. Oral appliance 600 includes arched frames 605. Arched frames 605 define slots 610. Slots 610 may be located on the facial and lingual surfaces of arched frames 605. In this manner, slots 610 may be positioned proximate the facial and lingual surfaces of a user's dental arches when arched frames 605 are positioned in the user's mouth. In particular embodiments, slots 610 improve the flexibility of arched frames 605 when arched frames 605 are being molded based on a user's teeth.

As in previous embodiments, arched frames 605 are configured to be positioned proximate to the occlusal surface of a user's maxillary and mandibular arches such that the arched frames extend beyond the cuspids of the user's maxillary and mandibular arches when arched frames 605 are positioned in the user's mouth. Arched frames 605 may be coupled to each other by a mechanism.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. An oral appliance comprising:
   an upper arched frame configured to be positioned within a user's mouth proximate the user's upper dentition when the upper arched frame is positioned in the user's mouth, the upper arched frame comprising a first tab and a second tab, the first tab and the second tab being positioned, with respect to each other, on opposite sides of a plane substantially bisecting the upper arched frame, wherein the upper arched frame does not deform when heated to 100 degrees Celsius;
   an upper moldable tray coupled to the upper arched frame such that the upper moldable tray extends beyond the cuspids of the user's upper dentition when the upper arched frame is positioned in the user's mouth, the upper moldable tray configured to deform when heated such that the upper moldable tray is configured to receive the user's upper dentition, the upper moldable tray comprising polycaprolactone;
   a lower arched frame configured to be positioned within the user's mouth proximate the user's lower dentition when the lower arched frame is positioned in the user's mouth, the lower arched frame comprising a third tab extending from the lower arched frame, wherein a coupling between the first tab and the third tab exerts a tensile force on the lower arched frame that pulls the lower arched frame in an anatomically anterior direction in the user's mouth, wherein the third tab is distal to the first tab when the upper arched frame and the lower arched frame are positioned in the user's mouth, wherein the lower arched frame does not deform when heated to 100 degrees Celsius; and
   a lower moldable tray coupled to the lower arched frame such that the lower moldable tray extends beyond the cuspids of the user's lower dentition when the lower arched frame is positioned in the user's mouth, the lower moldable tray configured to deform when heated such that the lower moldable tray is configured to receive the user's lower dentition, the lower moldable tray comprising polycaprolactone.

2. The oral appliance of claim 1, further comprising a seal configured to couple to the upper arched frame at the first and second tabs and configured to couple to the lower arched frame at the third tab.

3. The oral appliance of claim 2, wherein a first portion of the seal configured to be positioned proximate the upper arched frame is thicker than a second portion of the seal configured to be positioned proximate the lower arched frame.

4. The oral appliance of claim 2, wherein the seal is configured to be positioned between the user's dentition and the user's lips when the oral appliance is positioned in the user's mouth.

5. The oral appliance of claim 2, wherein the seal comprises a first cavity configured to engage the first tab, a second cavity configured to engage the second tab, and a third cavity configured to engage the third tab.

6. The oral appliance of claim 2, wherein the seal is further configured to extend beyond the cuspids of the user's upper dentition when the seal is positioned in the user's mouth.

7. The oral appliance of claim 1, wherein the first and second tabs extend from the upper arched frame in a buccal direction.

8. The oral appliance of claim 1, wherein the third tab extends from the lower arched frame in a buccal direction.

9. The oral appliance of claim 1, wherein the third tab is configured to engage a cavity to create the coupling.

10. The oral appliance of claim 1, further comprising a coupler configured to couple the upper arched frame to the lower arched frame and to establish a position of the user's lower dentition relative to the user's upper dentition when the upper and lower arched frames are positioned in the user's mouth.

11. The oral appliance of claim 1, wherein the upper arched frame is configured to extend beyond the cuspids of the user's upper dentition when the upper arched frame is positioned within the user's mouth.

* * * * *